US010646850B2

(12) United States Patent
Kanda et al.

(10) Patent No.: US 10,646,850 B2
(45) Date of Patent: May 12, 2020

(54) MATERIAL FOR BLOOD PURIFICATION

(71) Applicant: TORAY INDUSTRIES, INC., Tokyo (JP)

(72) Inventors: Shungo Kanda, Otsu (JP); Hiroshi Takahashi, Otsu (JP); Naotoshi Tomita, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 16/327,188

(22) PCT Filed: Sep. 8, 2017

(86) PCT No.: PCT/JP2017/032397
§ 371 (c)(1),
(2) Date: Feb. 21, 2019

(87) PCT Pub. No.: WO2018/047929
PCT Pub. Date: Mar. 15, 2018

(65) Prior Publication Data
US 2019/0184371 A1   Jun. 20, 2019

(30) Foreign Application Priority Data

Sep. 9, 2016   (JP) .................................. 2016-176289

(51) Int. Cl.
*B01J 20/26* (2006.01)
*A61M 1/36* (2006.01)
(Continued)

(52) U.S. Cl.
CPC .......... *B01J 20/265* (2013.01); *A61M 1/3679* (2013.01); *B01D 15/3828* (2013.01);
(Continued)

(58) Field of Classification Search
CPC . A61M 1/3679; B01D 15/3828; B01J 20/265; B01J 20/28023; B01J 20/3219;
(Continued)

(56) References Cited

U.S. PATENT DOCUMENTS 5,407,581 A * 4/1995 Onodera ............ B01D 39/1623
210/321.69
6,260,715 B1   7/2001 Simard et al.
(Continued)

FOREIGN PATENT DOCUMENTS

EP   0819439 A1   1/1998
EP   1439212 A1   7/2004
(Continued)

OTHER PUBLICATIONS

International Search Report, issued in PCT/JP2017/032397, PCT/ISA/210, dated Dec. 5, 2017.
(Continued)

*Primary Examiner* — Ana M Fortuna
(74) *Attorney, Agent, or Firm* — Birch, Stewart, Kolasch & Birch, LLP

(57) ABSTRACT

An object of the present invention is to provide a material for blood purification having the capability to remove cytokines and activated leukocyte-activated platelet complexes. The present invention provides a material for blood purification, the material containing a water-insoluble material in which a ligand having an amide group(s) and an amino group(s) is bound to a substrate, wherein the content of the amide group(s) is 3.0 to 7.0 mmol per 1 g dry weight of the water-insoluble material; and wherein the content of the amino group(s) is 1.0 to 7.0 mmol per 1 g dry weight of the water-insoluble material.

24 Claims, 1 Drawing Sheet

(51) Int. Cl.
  *B01D 15/38* (2006.01)
  *B01J 20/28* (2006.01)
  *B01J 20/32* (2006.01)

(52) U.S. Cl.
  CPC ... *B01J 20/28016* (2013.01); *B01J 20/28023* (2013.01); *B01J 20/28038* (2013.01); *B01J 20/321* (2013.01); *B01J 20/3212* (2013.01); *B01J 20/3219* (2013.01); *B01J 20/3251* (2013.01); *B01J 20/3293* (2013.01); *B01J 20/3295* (2013.01)

(58) Field of Classification Search
  CPC .. B01J 20/3251; B01J 20/3293; B01J 20/261; B01D 20/3255
  See application file for complete search history.

(56) References Cited

U.S. PATENT DOCUMENTS

| | | | |
|---|---|---|---|
| 9,127,250 B2 | 9/2015 | Ogasawara et al. | |
| 2004/0226874 A1 | 11/2004 | Nanko et al. | |
| 2005/0063935 A1* | 3/2005 | Hirai | A61M 1/3679 424/78.08 |
| 2013/0220912 A1 | 8/2013 | Tomita et al. | |
| 2019/0184371 A1* | 6/2019 | Kanda | B01D 15/3828 |

FOREIGN PATENT DOCUMENTS

| | | |
|---|---|---|
| EP | 2223712 A1 | 9/2010 |
| EP | 2633872 A1 | 9/2013 |
| JP | 5-166706 A | 7/1993 |
| JP | 8-281100 A | 10/1996 |
| JP | 10-147518 A | 6/1998 |
| JP | 2003-201251 A | 7/2003 |
| JP | 2006-312804 A | 11/2006 |
| JP | 4035191 B2 | 1/2008 |
| JP | 4224621 B2 | 2/2009 |
| JP | 2009-95436 A | 5/2009 |
| JP | 2009-254695 A | 11/2009 |
| JP | 4591974 B2 | 12/2010 |
| JP | 2011-145 A | 1/2011 |
| JP | 2011-194014 A | 10/2011 |
| JP | 5824873 B2 | 12/2015 |
| JP | 2016-77466 A | 5/2016 |
| WO | WO 2012/033522 A1 | 3/2012 |
| WO | WO 2012/057185 A1 | 5/2012 |
| WO | WO 2012/094571 A1 | 7/2012 |
| WO | WO 2012/133399 A1 | 10/2012 |

OTHER PUBLICATIONS

Written Opinion of the International Searching Authority, issued in PCT/JP2017/032397, PCT/ISA/237, dated Dec. 5, 2017.
Extended European Search Report for European Application No. 17848867.2, dated Nov. 20, 2019.
Hack et al., "Interleukin-8 in Sepsis: Relation to Shock and Inflammatory Mediators," Infection and Immunity, vol. 60, No. 7, Jul. 1992, pp. 2835-2942.
Nakada et al., "Continuous Hemodiafiltration with PMMA Hemofilter in the Treatment of Patients with Septic Shock," Mol Med, vol. 14, No. 5-6, May-Jun. 2006, pp. 257-263.
Oda et al., "Sequential measurement of IL-6 blood levels in patients with systemic inflammatory response syndrome (SIRS)/sepsis," Cytokine, vol. 29, 2005, pp. 169-175.
Zarbock et al., "Complete reversal of acid-induced acute lung injury by blocking of platelet-neutrophil aggregation," The Journal of Clinical Investigation, vol. 116, No. 12, Dec. 2006, pp. 3211-3219.
International Search Report for International Application No. PCT/JP2018/021655, dated Sep. 11, 2018.
Written Opinion of the International Searching Authority for International Application No. PCT/JP2018/021655, dated Sep. 11, 2018.

* cited by examiner

MATERIAL FOR BLOOD PURIFICATION

TECHNICAL FIELD

The present invention relates to a material for blood purification.

BACKGROUND ART

In recent years, there have been advances in the technology of blood purification, particularly the technology of removing humoral factors from blood, for the purposes of treatment of inflammatory diseases or pretransplant immunosuppression.

In Patent Document 1, an approach is made in which a water-insoluble material is used as a material for removing or inactivating cytokines that are one kind of proteins, in which water-insoluble material, a urea bond and an amino group; or a urea bond, an amide group, and an amino group; or an amide group, an amino group, and a hydroxyl group are introduced on a substrate composed of a polymer material.

Patent Document 2 discloses a water-insoluble material in which an amide group and an amino group suitable for removing high-mobility group proteins are introduced. The Patent Document 2 reports that an amino group content which is too small does not afford desired adsorptive performance, and an amino group content which is too large deteriorates the physical strength of the water-insoluble carrier and also tends to reduce the adsorptive performance, and accordingly, the content is preferably 0.03 µmol to 1 mmol, more preferably 0.1 µmol to 0.1 mmol, per 1 g weight of the water-insoluble carrier.

Patent Document 3 discloses a material for blood purification, in which 50 µm or less fibers are used. The Patent Document 3 reports that an amino group content which is too small tends not to express the function of the group, and an amino group content which is too large tends to reduce the physical strength of the fabric structure, and accordingly, the content is preferably 0.01 to 2.0 mol, more preferably 0.1 to 1.0 mol, per a repeating unit of the polymer.

In Patent Document 4, as for a separation membrane for artificial kidneys, an attempt has been made to increase an adsorption amount of an oxidized LDL by grafting a hydrophilic polymer containing an amide group, and polyethyleneimine on the surface of a substrate.

Here, cytokines refer to a group of proteins which, through a stimulus such as infection or trauma, are produced from various cells such as immunocompetent cells, released extracellularly, and allowed to act. Many are known, including interferon-α, interferon-β, interferon-γ, interleukin-1β, interleukin-1 to interleukin-15, tumor necrosis factor-α, tumor necrosis factor-β, high-mobility group box-1, erythropoietin, monocyte chemotactic factors, and the like. Cytokines are considered to be originally substances that organisms produce for biophylaxis, but it has been made clear that a group of proteins such as tumor necrosis factor-β, interleukin-6, interleukin-8, and monocyte chemotactic and activating factors, when excessively produced, get involved with tissue damage and pathology in various inflammatory diseases. For example, there is a report that administering tumor necrosis factor-β to an animal induces septic shock, and accordingly it is useful for improvement of pathology to inhibit the action of the tumor necrosis factor.

In the case of hypercytokinemia (for example, human sepsis), in which a high concentration of free cytokines are present in blood, the concentrations of interleukin-6 and interleukin-8 in blood increase remarkably (Non Patent Document 1 and Non Patent Document 2), and it is recognized that the concentrations of these in blood correlate with pathology and prognosis. In addition, it is pointed out that, in autoimmune diseases such as rheumatoid arthritis, allergic diseases, and the like, excessive production of interleukin-6 and interleukin-8 is involved with pathology.

On the other hand, in order to treat the above-mentioned inflammatory diseases by inhibiting the action of cytokines, an attempt has been made to administer to a living body a protein, such as typified by an antibody or a soluble receptor, that specifically binds to a target cytokine to inhibit its action; or a protein, such as a receptor antagonist, that binds to the receptor of a cytokine competitively with the cytokine.

In Non Patent Document 3, an attempt is made to remove cytokines from blood with a blood purification therapy using an artificial kidney.

Furthermore, recent interest has focused on an activated leukocyte-activated platelet complex as a new causative substance of inflammatory diseases. It is reported that the activated leukocyte-activated platelet complexes have a higher chemotactic activity to tissues exhibiting an inflammatory reaction compared with an activated leukocytes alone, and release more histotoxic substances, and that the interaction between an activated platelet and an activated leukocyte increases the release of histotoxic substances by the activated leukocyte (Non Patent Document 4).

PRIOR ART DOCUMENTS

Patent Documents

Patent Document 1: JP 4591974 B2
Patent Document 2: JP 5824873 B2
Patent Document 3: JP 5293599 B2
Patent Document 4: JP 4534486 B2

Non Patent Documents

Non Patent Document 1: Oda et al., Cytokine, 29, 169-175 (2005)
Non Patent Document 2: Hack et al., INFECT. IMMUN., 60, 2835-2842 (1992)
Non Patent Document 3: Hirasawa et al., MOL. MED., 14, 257-263 (2008)
Non Patent Document 4: Zarbock et al., J. Clin. Invest., 116, 3211-3219 (2006)

SUMMARY OF INVENTION

Problem to be Solved by the Invention

However, there is a problem in that conventional water-insoluble materials having an amide group and an amino group introduced therein contain a smaller amount of the amide group per 1 g of the water-insoluble material, and that the amino group content is also not sufficient to express blood purification performance. Patent Document 1 does not report an amide group content nor an amino group content suitable to remove cytokines. Patent Document 2 and 3 has no description related to an amide group content, discloses no example having an amide group introduced in Examples, and reports that introducing a larger amount of an amino group than 1 mmol per 1 g of a water-insoluble material reduces cytokine removal performance. In addition, no mention is made of activated leukocyte-activated platelet complexes, still less of a technology related to removal of activated leukocyte-activated platelet complexes.

Patent Document 4 discloses a separation membrane in which a hydrophilic polymer containing an amide group and a cationic polymer are immobilized on the surface of a substrate by γ-ray cross-linking, but the amino group and the amide group are not covalently bound in the separation membrane, and sufficient blood purification performance is not expressed at present. In addition, these documents neither disclose nor suggest that increasing the amide group and amino group contents is effective to enhance blood purification performance. Moreover, no mention is made of activated leukocyte-activated platelet complexes, still less of a technology related to removal of the activated leukocyte-activated platelet complexes.

There is also a problem in that preparing a large amount of protein for in vivo administration is very costly, and that if a protein to be administered is a foreign substance to organisms, it may induce an immunoreaction detrimental to patients.

As mentioned in Non Patent Document 3, it is pointed out that a blood purification therapy using an artificial kidney results in insufficient removal of cytokine. In addition, artificial kidneys generally cannot remove blood corpuscle components, and therefore it is difficult to remove activated leukocyte-activated platelet complexes.

Under these circumstances, there is a demand for a material that can remove not only cytokines but also activated leukocyte-activated platelet complexes in blood purification applications.

In view of these, an object of the present invention is to provide a material for blood purification that can remove cytokines and activated leukocyte-activated platelet complexes.

Means for Solving the Problems

As a result of intensive study to solve the problems described above, the present inventors discovered the following (1) to (8).

(1)
A material for blood purification, the material comprising a water-insoluble material in which a ligand having an amide group(s) and an amino group(s) is bound to a substrate, wherein the content of the amide group(s) is 3.0 to 7.0 mmol per 1 g dry weight of the water-insoluble material; and wherein the content of the amino group(s) is 1.0 to 7.0 mmol per 1 g dry weight of the water-insoluble material.

(2)
The material for blood purification, according to (1), wherein the ligand having the structure represented by Formula (I) below is bound to the substrate:

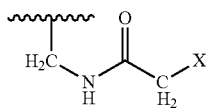
(I)

(wherein X is an amino group; and the wavy line represents a position at which the ligand is bound to the substrate).

(3)
The material for blood purification, according to (1) or (2), wherein the ligand has a phenyl group, and the ligand having the structure represented by Formula (II) below is bound to the substrate:

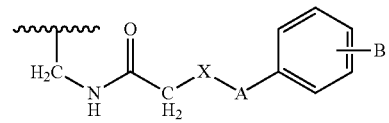

(wherein X is an amino group; A is a linker; B is a hydrogen atom or halogen atom; and the wavy line represents a position at which the ligand is bound to the substrate); and wherein the content of the phenyl group is more than 0 mmol and not more than 7.0 mmol per 1 g dry weight of the water-insoluble material.

(4)
The material for blood purification, according to any one of (1) to (3), wherein the substrate is a polystyrene or polysulfone, or a derivative thereof.

(5)
The material for blood purification, according to any one of (1) to (4), wherein the material is in the form of fibers or particles.

(6)
The material for blood purification, according to any one of (1) to (5), wherein the material is in the form of a knitted fabric having an opening ratio of 0.1 to 30.0%.

(7)
The material for blood purification, according to any one of (1) to (6), wherein the material is for removing a cytokine and an activated leukocyte-activated platelet complex.

(8)
An apparatus for blood purification, the apparatus comprising the material for blood purification, according to any one of (1) to (7).

Effect of the Invention

The material for blood purification according to the present invention can remove cytokines and activated leukocyte-activated platelet complexes, so that the material can be used as a carrier for blood purification.

MODE FOR CARRYING OUT THE INVENTION

Figure 1:
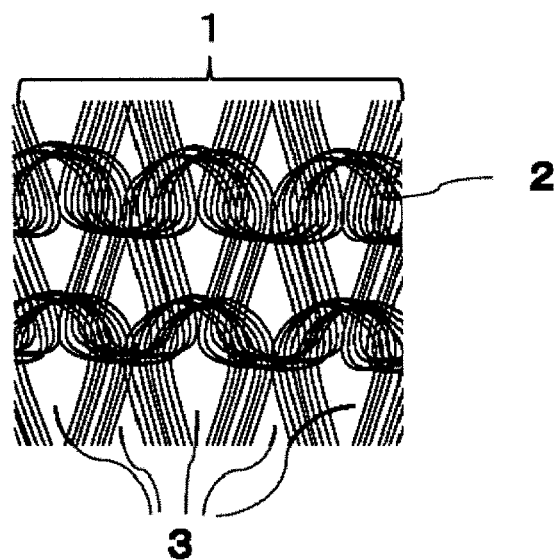
FIG. 1 is a view showing the opening portions and the non-opening portions in the material for blood purification in the form of a knitted fabric.

The present invention will now be described in detail.

The material for blood purification according to the present invention is characterized by comprising a water-insoluble material in which a ligand having an amide group(s) and an amino group(s) is bound to a substrate, wherein the content of the amide group(s) is 3.0 to 7.0 mmol per 1 g dry weight of the water-insoluble material; and wherein the content of the amino group(s) is 1.0 to 7.0 mmol per 1 g dry weight of the water-insoluble material.

The term "ligand" means a chemical structure contained in a water-insoluble material to afford blood purification performance.

The term "substrate" means a material to which a ligand having an amide group(s) and an amino group(s) can be immobilized by chemical modification and which is water-insoluble after the immobilization of the ligand having an amide group(s) and an amino group(s). For example, the substrate is a polymer material having, in the repeating structures, a functional group reactive with a carbon cation, such as an aromatic ring or a hydroxyl group, and may be: a synthetic polymer material such as a poly(aromatic vinyl compound) (for example, polystyrene), a polyester (for example, polyethylene terephthalate, polybutylene terephthalate), polysulfone, or polyvinyl alcohol; a natural polymer material such as cellulose, collagen, chitin, chitosan, or dextran; or a derivative in which an alkyl group, halogen group, halogenated alkyl group, acetal group, ether group, or the like is imparted to the synthetic polymer material or natural polymer material. Examples of polystyrene derivatives include poly(p-chloromethylstyrene), poly (α-methylstyrene), poly(β-methylstyrene), poly(p-tert-butoxystyrene), poly(p-acetoxystyrene), and poly(p-(1-ethoxyethoxy)styrene). Although the composition of each of these polymer materials is not limited to a particular one, homopolymers or copolymers between the above-mentioned polymers may be used, or a plurality of the above-mentioned polymer materials may be physically blended and used. In particular, for blood purification, materials not having a hydroxyl group are preferable: poly(aromatic vinyl compounds) (for example, polystyrene) or derivatives thereof; polyesters (for example, polyethylene terephthalate and polybutylene terephthalate) or derivatives thereof; and polysulfone or derivatives thereof. More preferable materials are polystyrene or polysulfone or derivatives thereof; in other words, polystyrene or derivatives thereof, or polysulfone or derivatives thereof. Among these, polystyrenes or derivatives thereof are still more preferable in that they have many aromatic rings per unit weight and easily undergo introduction of a ligand having an amide group(s) and an amino group(s).

The polymer material used for the substrate may have a cross-linked structure to express water-insolubility after the immobilization of the ligand. There is no limitation to the cross-linked structure. A preferable material is, for example, a polymer material in which a cross-linked structure is introduced by copolymerizing a bifunctional monomer such as divinylbenzene, or a polymer material in which a cross-linked structure is introduced by reacting a cross-linker such as aldehyde with a functional group such as an aromatic ring or hydroxyl group in the polymer material. In the light of easy procurement, a more preferable material is a polymer material in which a cross-linked structure is introduced by reacting a bifunctional compound with a functional group such as an aromatic ring or hydroxyl group in the polymer material, and using formaldehyde as a cross-linker is still more preferable.

The term "water-insoluble material" is a material insoluble in water. Here, being insoluble in water means that the dry weight of a water-insoluble material changes by 1% or less between before and after the material is put in water. This dry weight change is a ratio of the dry weight of a solid content to the dry weight of a water-insoluble material that is yet to be immersed in water, wherein the material is immersed, for one hour, in an amount of 37° C. water that is nine times larger than the dry weight of the material, the material is then pulled out using tweezers and the like, the remaining water is dried in vacuum at 50° C. or less, and the solid content is left behind. A material which is not made insoluble poses a risk of increasing the amount of eluate when the material is actually used, which is not preferable from a safety point of view.

The term "dry weight" means the weight of a solid in a dry state. Here, a solid in a dry state means a solid in a state in which the amount of liquid component contained in the solid is 1 wt % or less. When a solid is measured for weight and then dried by heating at 80° C. at atmospheric pressure for 24 hours, and the weight reduction of the remaining solid compared with the weight of the solid before drying is 1 wt % or less, the solid is considered to be in a dry state.

The term "material for blood purification" means a material including at least a water-insoluble material as a part of the material for blood purification, and includes a material composed of a water-insoluble material alone and a material in which a water-insoluble material is fixed to or mixed with a suitable reinforcing material. The operation of the fixing or mixing may be carried out before or after the material is formed into a shape.

The chemical structure of the reinforcing material is not particularly limited, and examples of reinforcing materials include a polymer material not having an aromatic ring or a hydroxyl group in the repeating structure, for example, homopolymers or copolymers of polyamide, polyacrylonitrile, polyethylene, polypropylene, nylon, polymethylmethacrylate, or polytetrafluoroethylene; or materials obtained by physically blending the above-described homopolymers and/or the copolymers; and the like. Among these, polyethylene and polypropylene are preferable.

The term "amide group" means an amide bond included in a ligand, may be any amide bond of a primary amide, secondary amide, and tertiary amide, and is preferably a secondary amide. At least one of the amide groups included in a ligand is preferably covalently bound to a substrate via an alkylene group. Examples of preferable alkylene groups include a methylene group, ethylene group, propylene group, and the like, and a methylene group is more preferable.

The term "amino group" means a chemical structure having one or more amines as a partial structure, and examples of amino groups include amino groups derived from ammonia; amino groups derived from primary amines such as aminomethane, aminoethane, aminopropane, aminobutane, aminopentane, aminohexane, aminoheptane, aminooctane, and aminododecane; amino groups derived from secondary amines such as dimethylamine, diethylamine, dipropylamine, phenylethylamine, monomethylaminohexane, and 3-amino-1-propene; amino groups derived from tertiary amines such as triethylamine, phenyldiethylamine, and aminodiphenylmethane; and amino groups derived from compounds having a plurality of amino groups (hereinafter referred to as polyamines), such as ethylenediamine, diethylenetriamine, triethylenetetramine, tetraethylenepentamine, dipropylenetriamine, polyethyleneimine (having a weight average molecular weight of 500 to 100000), N-methyl-2,2'-diaminodiethylamine, N-acetylethylenediamine, and 1,2-bis(2-aminoethoxyethane). Among these, amino groups derived from polyamines having high molecular mobility are suitable for blood purification because such amino groups easily come in contact with blood components, but if the amino groups have a large molecular weight, the amino groups themselves have large steric hindrance and reduce the blood purification performance. Therefore, it is preferable that the polyamine contains 2 to 7 amino groups and that the whole polyamine has a straight-chain structure. For example, amino groups derived from ethylenediamine, diethylenediamine, triethylenediamine, diethylenetriamine, triethylenetriamine, tetraethylenetriamine, triethylenetetramine, tetraethylenetetramine, pentaethylenetetramine, tetraethylenepentamine, pentaethylenepentamine, hexaethylenepentamine, pentaethylenehexamine, hexaethylenehexamine, heptaethylenehexamine, hexaethyleneheptamine, heptaethyleneheptamine, or octaethyleneheptamine are preferable. Amino groups derived from ethylenediamine, diethylenetriamine, triethylenetetramine, tetraethylenepentamine, pentaethylenehexamine, or polyethyleneimine are preferable. Amino groups derived from tetraethylenepentamine are more preferable. In addition, the amino groups are more preferably amino groups derived from primary or secondary amines.

The number of carbon atoms per one nitrogen atom of the amino group included in a ligand is preferably 18 or less, more preferably 14 or less, still more preferably 8 or less, considering nucleophilicity and steric hindrance that affect a reaction ratio. In this regard, the nitrogen atom of the amino group is preferably substituted with an alkyl group. The structure of the alkyl group may be a hydrocarbon group having a straight-chain, branched, or cyclic structure. Among others, the structure is preferably a straight-chain alkyl group such as a methyl group, ethyl group, propyl group, butyl group, pentyl group, hexyl group, heptyl group, or octyl group, and more preferably a methyl group, ethyl group, or propyl group.

The content of the amide group(s) per 1 g dry weight of the water-insoluble material is 3.0 to 7.0 mmol in the light of the performance of removal of humoral factors from blood and the limit of the substitution ratio to aromatic rings. The content the amide group(s) is preferably 4.0 to 7.0 mmol, more preferably 5.0 to 7.0 mmol. Any preferable lower limit can be combined with any preferable upper limit.

The content of the amino group(s) per 1 g dry weight of the water-insoluble material is 1.0 to 7.0 mmol because the content which is too low reduces the performance, and the content which is too high reduces the efficiency of introduction reaction. The content is preferably 1.0 to 5.0 mmol, more preferably 2.0 to 4.0 mmol. Any preferable lower limit can be combined with any preferable upper limit. In this regard, the content of the amide group(s) per 1 g dry weight of the water-insoluble material and the content of the amino group(s) per 1 g dry weight of the water-insoluble material may be combined in any way. For example, it is preferable that the content of the amide group(s) per 1 g dry weight of the water-insoluble material is 3.0 to 7.0 mmol, and the content of the amino group(s) per 1 g dry weight of the water-insoluble material is 1.0 to 5.0 mmol. It is more preferable that the content of the amide group(s) per 1 g dry weight of the water-insoluble material is 4.0 to 7.0 mmol, and the content of the amino group(s) per 1 g dry weight of the water-insoluble material is 2.0 to 4.0 mmol.

The term "ligand having an amide group(s) and an amino group(s)" means a ligand in which the amide group(s) and the amino group(s) are covalently bound via an alkylene group. An amide group controls the electron density of an amino group, and therefore the alkylene group preferably has a saturated hydrocarbon structure having 5 or less carbon atoms. Examples of alkylene groups include a pentylene group, butylene group, propylene group, ethylene group, and methylene group. A methylene group is more preferable. In addition, the ligand having an amide group(s) and an amino group(s) is preferably such that the amide group side is bound to a substrate. There is no particular limitation to the included functional group other than the amide group and the amino group, and the ligand may contain, for example, a phenyl group (the phenyl group may have a substituent such as a halogen atom, halogenated alkyl group, and a $C_1$-$C_5$ straight-chain alkyl group). In this case, the phenyl group is preferably bound to an amino group via the below-mentioned linker.

The term "water-insoluble material in which a ligand having an amide group(s) and an amino group(s) is bound to a substrate" is synonymous with a water-insoluble material in which a ligand having an amide group(s) and an amino group(s) and a substrate are bound, and encompasses both a water-insoluble carrier in which a ligand having an amide group(s) and an amino group(s) is directly bound to a substrate; and a water-insoluble carrier in which the ligand is indirectly bound to a substrate via a spacer such as an alkylene group.

Table 1 shows examples of modes of structures resulting from the binding of a ligand having an amide group(s) and an amino group(s) to a substrate, and Tables 2-1 to 2-7 shows examples of preferable modes of structures resulting from the binding of a ligand having an amide group(s) and an amino group(s) to a substrate, although such modes are not limited to these examples.

TABLE 1

Structural Formula

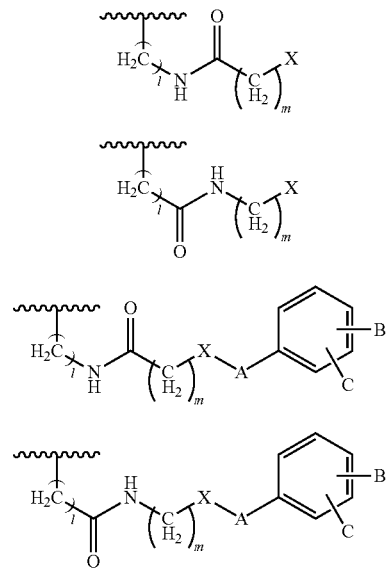

In Table 1, l represents an integer of 0 to 5, m represents an integer of 0 to 5, X represents an amino group, A represents a linker, B represents a hydrogen atom or halogen atom, C represents a hydrogen atom or halogen atom, and the wavy line represents a position at which the ligand is bound to the substrate.

TABLE 2-1

Structural Formula

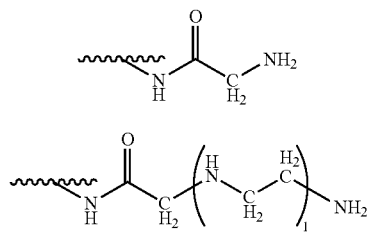

TABLE 2-1-continued

Structural Formula

TABLE 2-1-continued

Structural Formula

[Chemical structures showing various substituent groups with PEI and amine terminations]

TABLE 2-2

Structural Formula

[Chemical structures showing substituents with benzamide, chlorobenzamide, and phenylurea terminations]

TABLE 2-2-continued

Structural Formula

[Chemical structures showing substituents with chloro- and dichloro-benzamide and phenylurea terminations]

TABLE 2-2-continued

Structural Formula

TABLE 2-3

Structural Formula

TABLE 2-3-continued

Structural Formula (Chemical structures not transcribable as text.)

TABLE 2-3-continued
Structural Formula
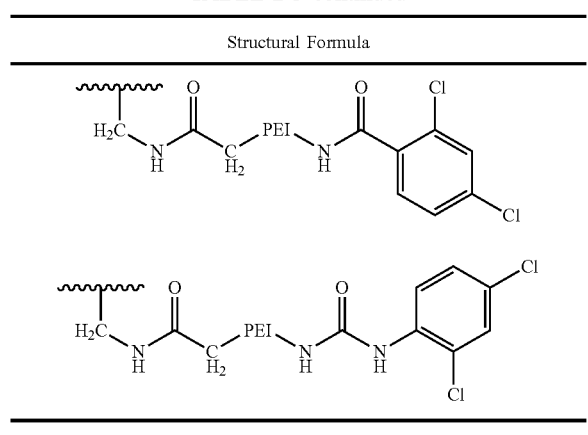
TABLE 2-4
Structural Formula
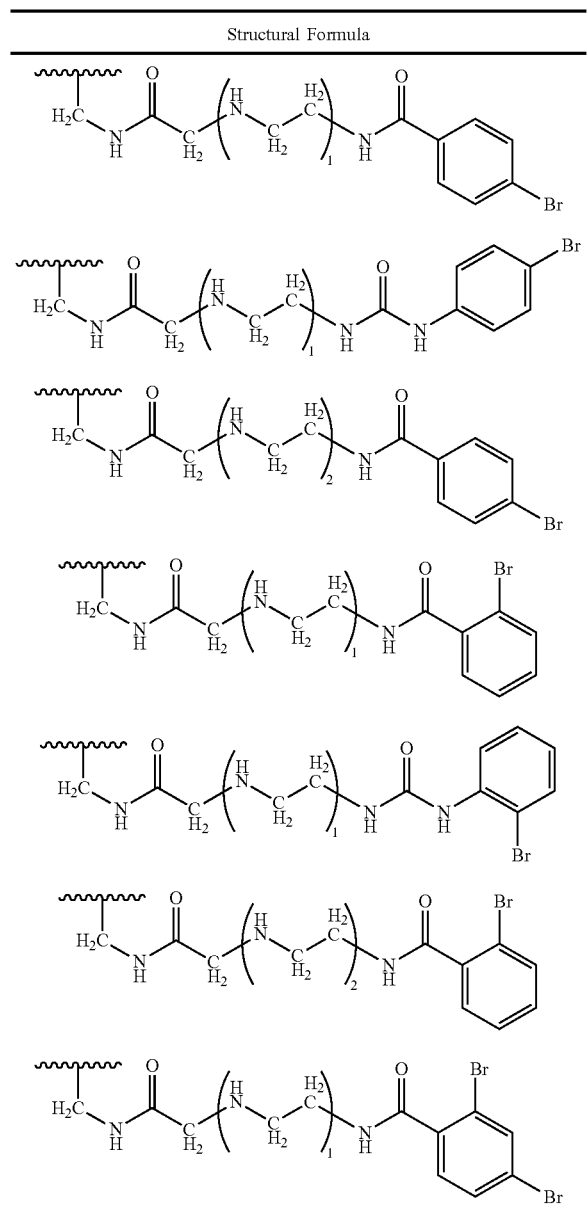
TABLE 2-4-continued
Structural Formula
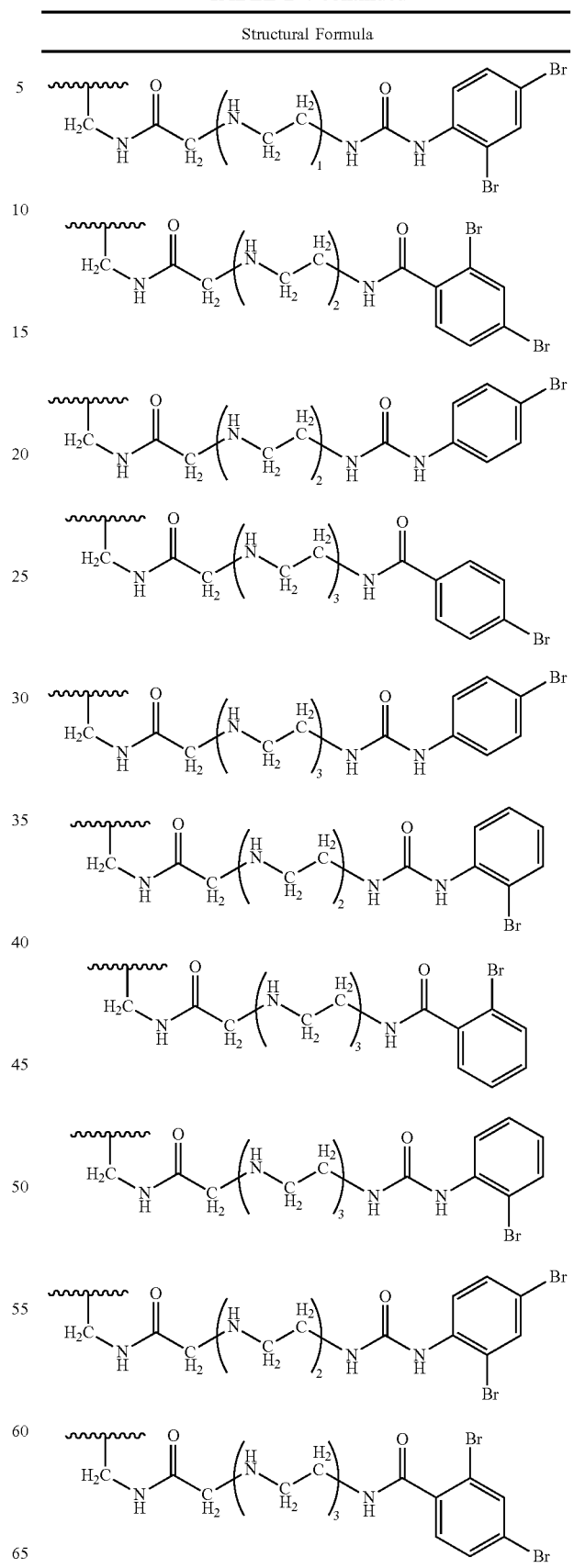

TABLE 2-4-continued
Structural Formula
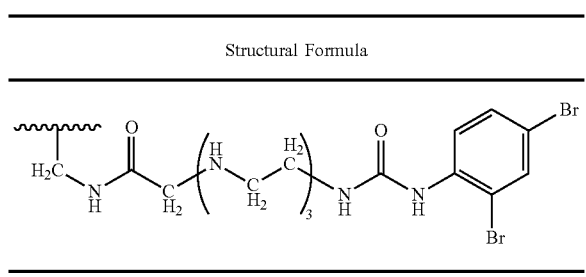
TABLE 2-5
Structural Formula
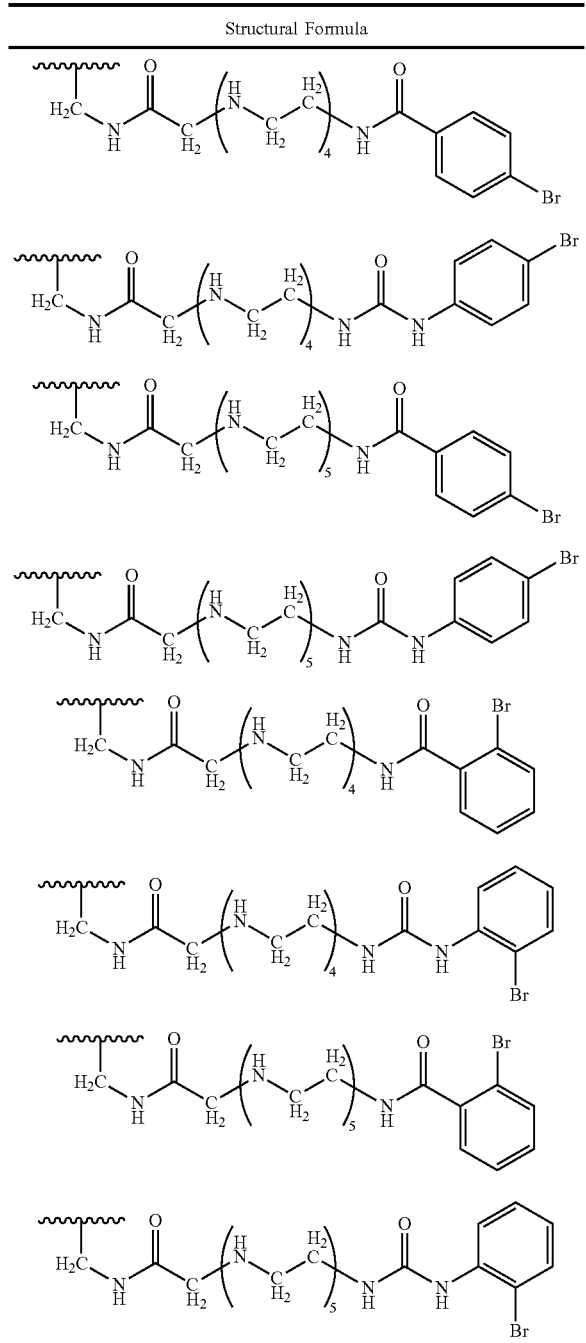
TABLE 2-5-continued
Structural Formula
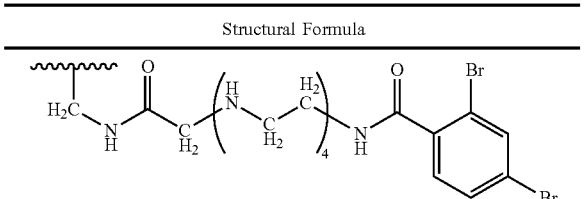
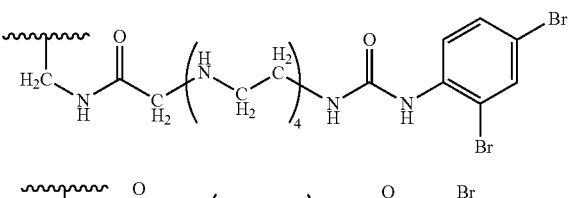
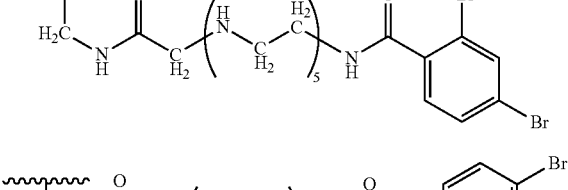
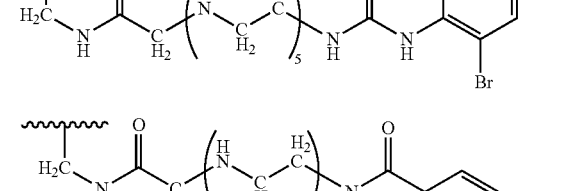
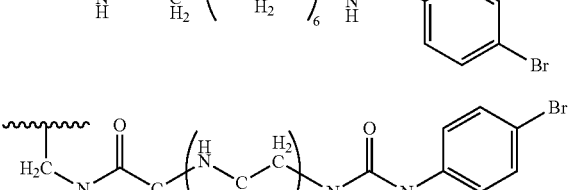
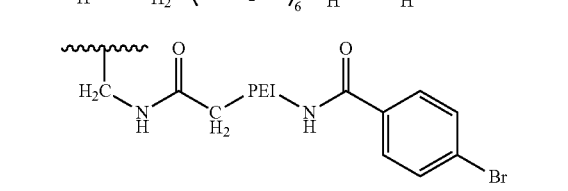
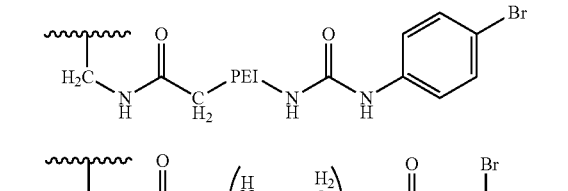
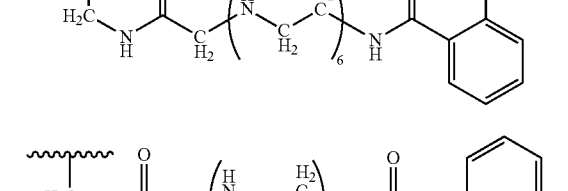

TABLE 2-5-continued
Structural Formula
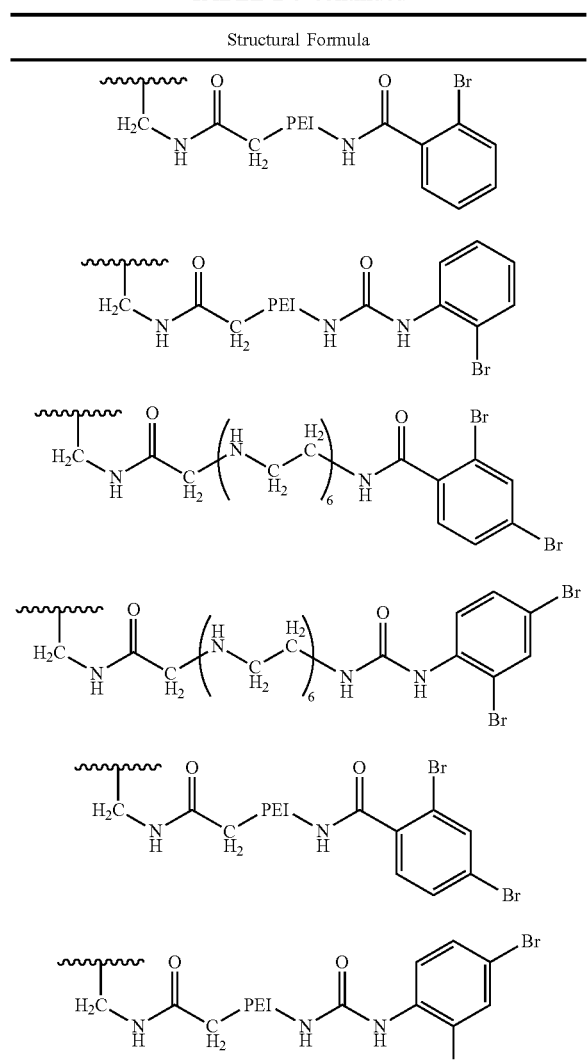
TABLE 2-6
Structural Formula
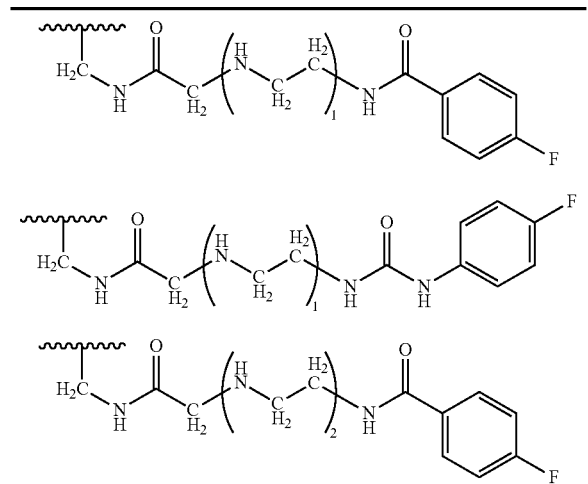
TABLE 2-6-continued
Structural Formula
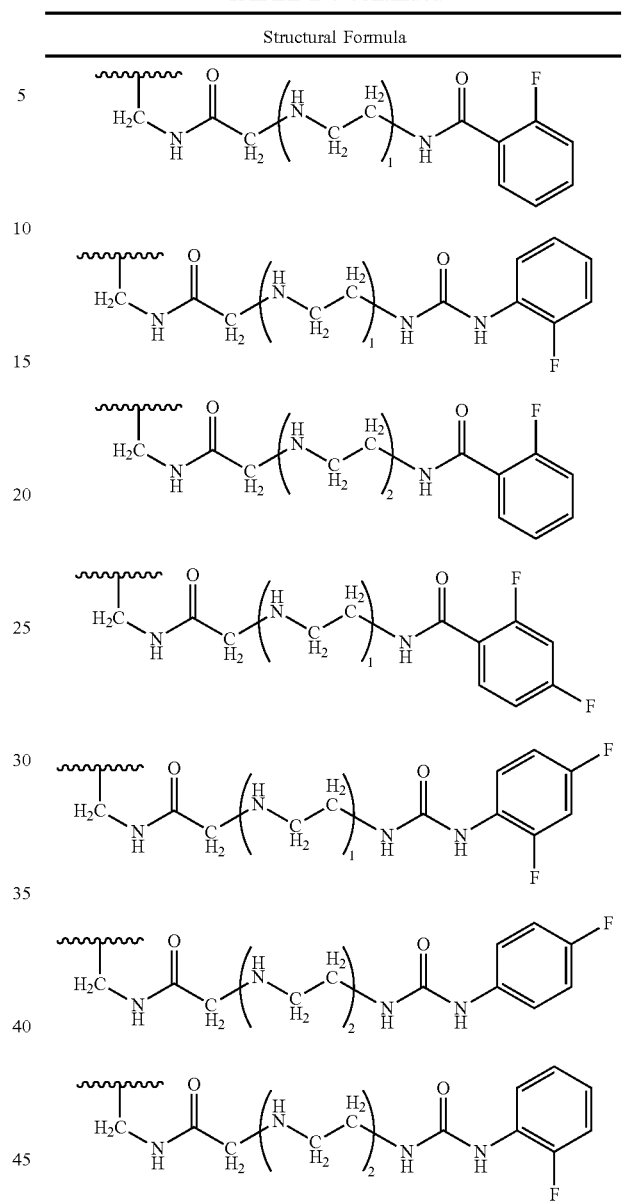

TABLE 2-6-continued

Structural Formula

[Chemical structures depicting variations of amide/urea compounds with fluorinated phenyl groups]

TABLE 2-7

Structural Formula

[Chemical structures depicting variations of amide/urea compounds with fluorinated phenyl groups]

TABLE 2-7-continued

Structural Formula

[Chemical structures depicting variations of amide/urea compounds with fluorinated phenyl groups]

TABLE 2-7-continued

Structural Formula

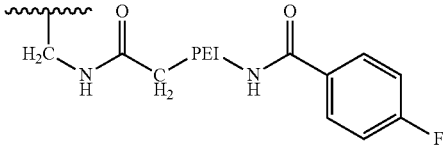
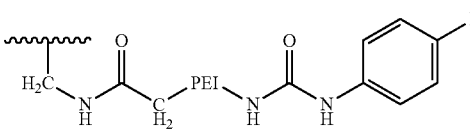
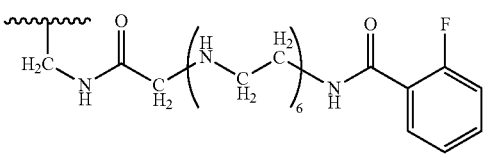
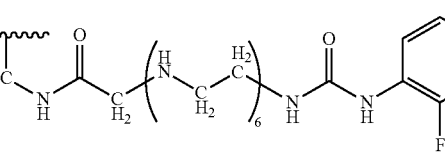
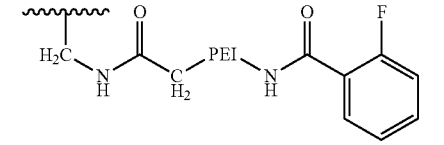
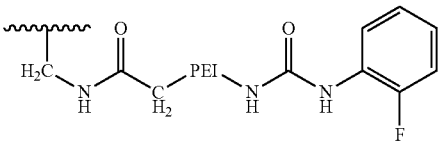
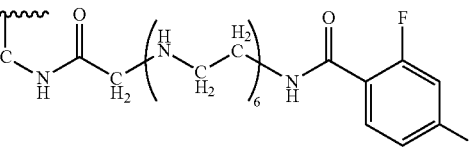
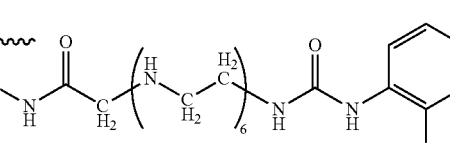
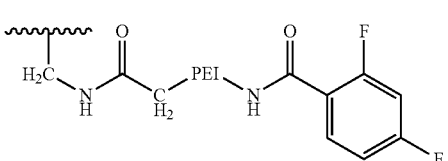

TABLE 2-7-continued

Structural Formula

In Table 2-1 to 2-7, PEI represents a polyethyleneimine having a weight average molecular weight of 600 to 100000, and the wavy line represents a position at which the ligand is bound to the substrate.

Examples of preferable modes of structures resulting from the binding of a ligand having an amide group(s) and an amino group(s) to a substrate in a water-insoluble carrier include a structure represented by the following Formula (I):

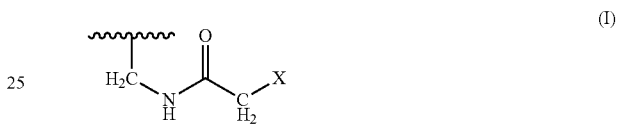

(I)

(wherein X is an amino group; and the wavy line represents a position at which the ligand is bound to the substrate).

X is preferably an amino group derived from a polyamine, and more preferably an amino group derived from ethylenediamine, diethylenetriamine, triethylenetetramine, tetraethylenepentamine, pentaethylenehexamine, or polyethyleneimine.

Specific examples of structures represented by the above-mentioned Formula (I) are shown in Table 3, but the structures are not limited to these examples.

TABLE 3

Structural Formula

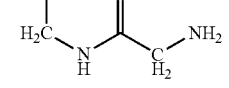
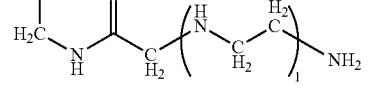
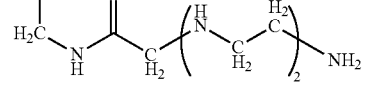
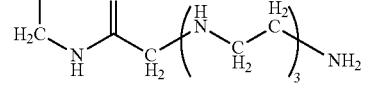
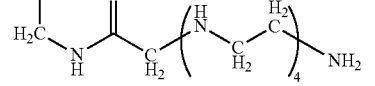

TABLE 3-continued

Structural Formula (chemical structures)

In Table 3, PEI represents a polyethyleneimine having a weight average molecular weight of 600 to 100000, and the wavy line represents a position at which the ligand is bound to the substrate.

Furthermore, a structure represented by the following Formula (II), in other words, a ligand having a phenyl group(s) in addition to an amide group(s) and an amino group(s) may be bound to a substrate, and is more preferable because binding of the structure can further inhibit the adhesion of platelets.

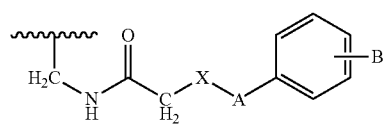

(II)

(wherein X is an amino group; A is a linker; B is a hydrogen atom or halogen atom; and the wavy line represents a position at which the ligand is bound to the substrate.)

X is preferably an amino group derived from a polyamine, and more preferably an amino group derived from ethylenediamine, diethylenetriamine, triethylenetetramine, tetraethylenepentamine, pentaethylenehexamine, or polyethyleneimine.

A is preferably an amide bond or urea bond.

B is preferably a hydrogen atom or chlorine atom.

It is preferable that X is an amino group derived from a polyamine, A is an amide bond or urea bond, and B is a hydrogen atom or chlorine atom.

Specific examples of structures represented by the above-mentioned Formula (II) are shown in Tables 4-1 to 4-6, but such structures are not limited to these examples.

TABLE 4-1

Structural Formula (chemical structures)

TABLE 4-1-continued

Structural Formula (chemical structures)

TABLE 4-1-continued

Structural Formula (structures)

TABLE 4-2

Structural Formula (structures)

TABLE 4-2-continued

Structural Formula (structures)

TABLE 4-2-continued

*(Structural formulas shown)*

TABLE 4-3

*(Structural formulas shown)*

TABLE 4-3-continued

Structural Formula (Structures omitted - chemical structural formulas)

TABLE 4-4

Structural Formula (Structures omitted - chemical structural formulas)

TABLE 4-4-continued

Structural Formula (Structures omitted - chemical structural formulas)

TABLE 4-4-continued
Structural Formula
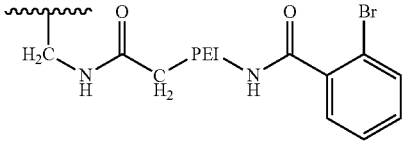
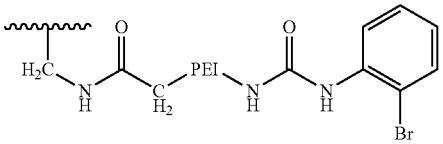
TABLE 4-5
Structural Formula
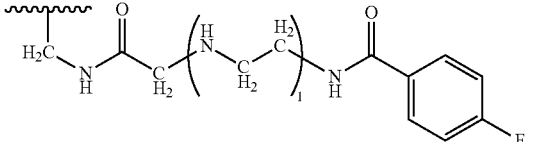
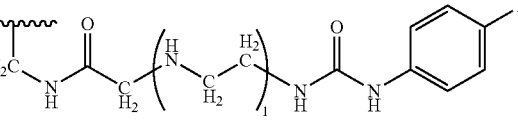
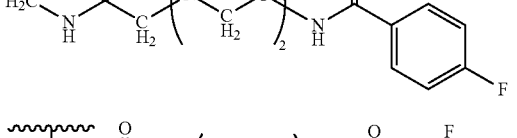
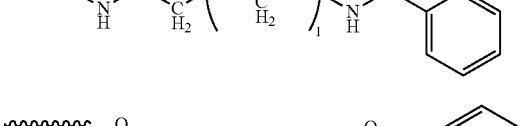
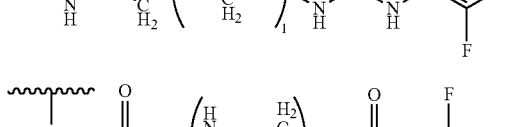
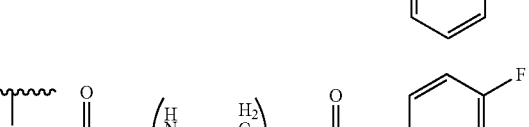
TABLE 4-5-continued
Structural Formula
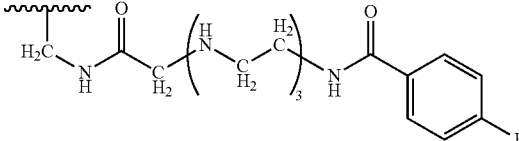
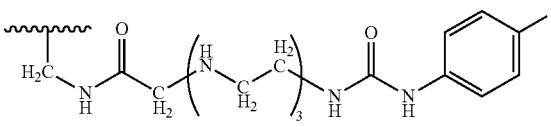
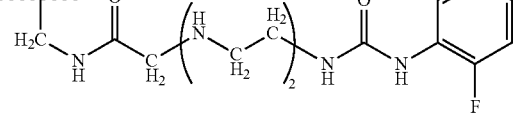
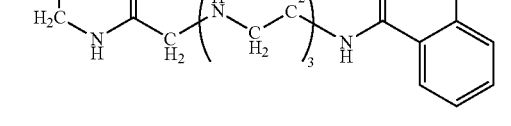
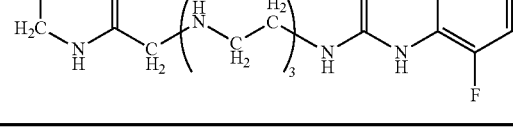
TABLE 4-6
Structural Formula
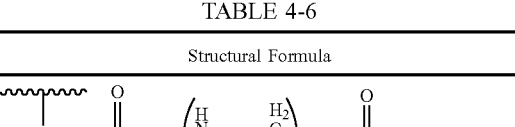
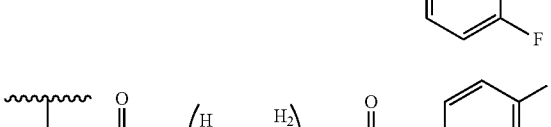
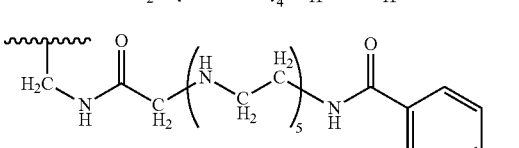
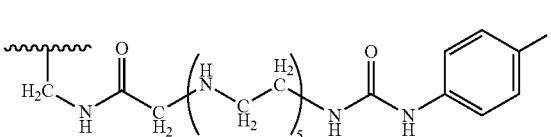

TABLE 4-6-continued

Structural Formula

[Chemical structures shown]

In Tables 4-1 to 4-6, PEI represents a polyethyleneimine having a weight average molecular weight of 600 to 100000, and the wavy line represents a position at which the ligand is bound to the substrate.

The phenyl group content that is too small does not express the effect of suppressing platelet adhesion, and the content that is too large reduces the performance of removal of humoral factors from blood. Therefore, the phenyl group content is preferably more than 0 mmol and not more than 7.0 mmol, preferably 0.01 to 7.0 mmol, more preferably 0.01 to 3.0 mmol, still more preferably 0.02 to 2.0 mmol, still more preferably 0.02 to 1.0 mmol, per 1 g dry weight of the water-insoluble material. Any preferable lower limit can be combined with any preferable upper limit. In this regard, the content of the phenyl group(s), the content of the amide group(s) per 1 g dry weight of the water-insoluble material, and the content of the amino group(s) per 1 g dry weight of the water-insoluble material may be combined in any way. For example, it is preferable that the content of the amide group(s) per 1 g dry weight of the water-insoluble material is 3.0 to 7.0 mmol, the content of the amino group(s) per 1 g dry weight of the water-insoluble material is 1.0 to 5.0 mmol, and the content of the phenyl group(s) per 1 g dry weight of the water-insoluble material is more than 0 and not more than 7.0 mmol. It is more preferable that the content of the amide group(s) per 1 g dry weight of the water-insoluble material is 4.0 to 7.0 mmol, the content of the amino group(s) per 1 g dry weight of the water-insoluble material is 2.0 to 4.0 mmol, and the content of the phenyl group(s) per 1 g dry weight of the water-insoluble material is 0.01 to 7.0 mmol. It is particularly preferable that the content of the amide group(s) per 1 g dry weight of the water-insoluble material is 5.0 to 7.0 mmol, the content of the amino group(s) per 1 g dry weight of the water-insoluble material is 2.0 to 4.0 mmol, and the content of the phenyl group(s) per 1 g dry weight of the water-insoluble material is 0.01 to 3.0 mmol/g.

The term "halogen atom" means a fluorine atom, chlorine atom, bromine atom, or iodine atom.

The term "phenyl group" means a phenyl group derived from an unsubstituted benzene or substituted benzene compound. Examples of phenyl groups include benzene, fluorobenzene, chlorobenzene, bromobenzene, 1,2-difluorobenzene, 1,2-dichlorobenzene, 1,2-bromobenzene, 1,3-difluorobenzene, 1,3-dichlorobenzene, 1,3-dibromobenzene, 1,4-difluorobenzene, 1,4-dichlorobenzene, 1,4-dibromobenzene, and the like. With a view to controlling the electric charge of the amino group, phenyl groups derived from halogenated benzenes having an electron-withdrawing group imparted thereto are preferable.

Among others, chlorophenyl groups derived from chlorobenzene are preferable. The electron-withdrawing group is preferably bound at the para position in the light of resonance structure, and in particular, a phenyl group derived from chlorobenzene is preferably a p-chlorophenyl group in which a linker and a chlorine atom are substituted at the para position.

The term "linker" means a chemical bond between the above-mentioned amino group and the above-mentioned phenyl group. Examples of linkers include electrically neutral chemical bonds such as an amide bond, urea bond, ether bond, or ester bond. An amide bond or urea bond is preferable.

The form of the material for blood purification according to the present invention is not limited to a particular one, and is preferably a fiber form or particle form, more preferably a fiber form. Furthermore, yarn bundles, yarn, net, knitted fabric, and woven fabric which are processed from fiber are preferable among the fiber forms, and yarn bundles, knitted fabric, and woven fabric are more preferable, considering the large surface area and small flow path resistance.

The single yarn diameter of the fiber may have any value, and is preferably 3 to 200 μm, more preferably 5 to 50 μm, still more preferably 10 to 40 μm, with a view to enhancing the contact area and maintaining the material strength. Any preferable lower limit can be combined with any preferable upper limit.

The term "single yarn diameter" means an average of diameters of single yarns of a fiber, wherein ten small piece samples are randomly taken from the fiber, each sample is photographed using a scanning electromicroscope at a magnification ratio of 1000× to 3000×, and the diameter value is measured at 10 points on each photograph (100 points in total).

Examples of the cross-section structure of the fiber include a single yarn composed of one kind of polymer or a composite fiber of a core-in-sheath type, sea-island type, or side-by-side type. Composite fibers are preferable, in which a reinforcing material is used for the core component, and an alloy of a substrate and a reinforcing material is used for the sheath component in the light of maintaining material strength in blood purification; multi-core sea-island type composite fibers are preferable, in which polyethylene terephthalate is used for the sea component in the light of spinning properties; and sea-island type composite fibers are preferable, in which a reinforcing material is used for the island component and an alloy of a substrate and a reinforcing material is used for the sea component. Furthermore, it is preferable that the reinforcing material is polypropylene and the substrate is polystyrene or a derivative thereof.

Among the materials for blood purification in the above-mentioned forms, knitted fabric, felt, and net can be produced by a known method using fibers as a raw material. Examples of methods of producing felt include a wet method, carding method, airlaying method, spun-bonding method, and meltblowing method. Examples of methods of producing knitted fabric and net include a plain weaving method and circular knitting method. In particular, knitted fabric produced by a circular knitting method is preferable in the light of a larger loading weight per unit volume and loading into an apparatus for blood purification.

Here, the opening ratio of the material for blood purification in the form of a knitted fabric is preferably 0.1 to 30.0%, more preferably 1.0 to 30.0%, particularly preferably 7.0 to 15.0%, in that the knitted fabric whose opening ratio is too large causes the fiber to unravel, complicates the flow path, and generates a pressure loss in blood purification, and that the knitted fabric whose opening ratio is too small gets clogged with protein and blood corpuscle components in blood, increases the pressure, and thus is unsuitable for blood purification. The lower limit of the opening ratio is preferably 0.1% or more, more preferably, 1% or more, particularly preferably 7.0% or more. The upper limit of the opening ratio is preferably 30.0% or less, more preferably 15.0% or less. Any preferable lower limit can be combined with any preferable upper limit.

The term "pressure loss" means a pressure difference between a pressure applied to blood to pass the blood perpendicularly through the material for blood purification in the form of a knitted fabric, and a pressure applied to the blood that has passed through the material for blood purification in the form of a knitted fabric. Specifically, blood is allowed to flow through the material for blood purification in the form of a knitted fabric, the inlet pressure and outlet pressure are each measured, and a value obtained by subtracting the outlet pressure value from the inlet pressure value is the pressure loss.

Blood purification poses a concern that generation of a pressure loss may increase pressure in blood purification, and for this reason, the pressure loss value is preferably 50 mmHg or less, more preferably 30 mmHg or less, particularly preferably 10 mmHg or less, wherein the pressure loss value is given by subtracting the outlet pressure value from the inlet pressure value, wherein blood is allowed to pass at 100 mL/min through the apparatus for blood purification which is loaded with the material for blood purification in the form of a knitted fabric.

Figure 2:
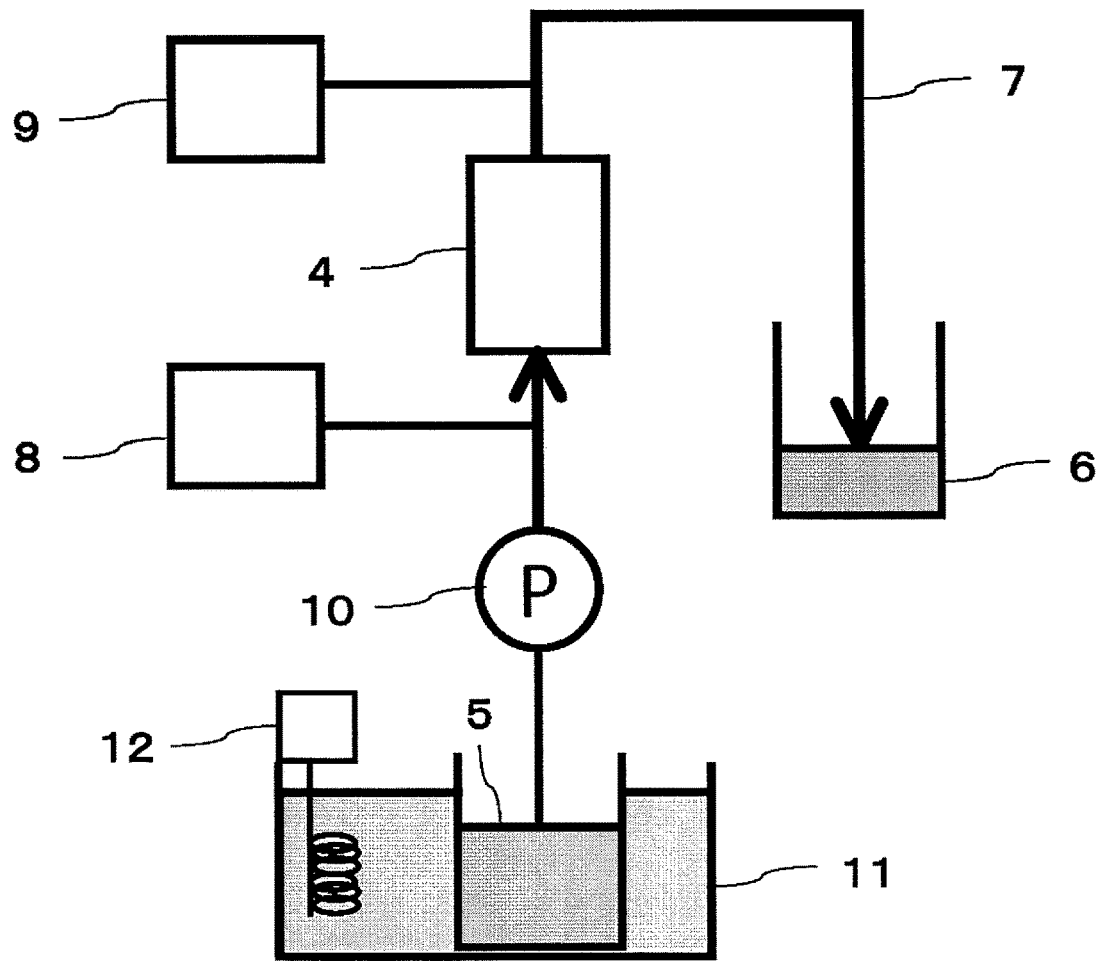
FIG. 2 is a schematic view of a circuit and a device used in a pressure loss measurement test.

A pressure loss of the material for blood purification in the form of a knitted fabric can be measured by laminating layers of the material for blood purification in the form of a knitted fabric and allowing simulated blood to pass through the laminate perpendicularly. In this regard, the simulated blood refers to a solution set so as to have the same rate of shear as that of human blood, and examples of the simulated blood include a 50 wt % glycerin aqueous solution. A specific measurement method will be described below. First, layers of the material for blood purification in the form of a knitted fabric are laminated in a container having an inlet and outlet at the top and bottom. The material for blood purification in the form of a knitted fabric is set to have a loading density of 0.30 g/cm$^3$ in the container. Next, simulated blood is allowed to pass through the container at a given flow rate, and the inlet pressure and outlet pressure are each measured. Then, a pressure loss can be determined by subtracting the outlet pressure value from the inlet pressure value. The flow rate (mL/min) of simulated blood in measurement is set on the basis of 100 mL/min per 145 cm$^3$ of container volume, taking clinical practice of blood purification into consideration. With a container having a volume of, for example, 5 cm$^3$, a measurement is carried out with the flow rate set at 100 mL/min/145 cm$^3$×5 cm$^3$=3.4 mL/min. A schematic view of a circuit and a device used in a pressure loss measurement test is shown in FIG. 2. In FIG. 2, simulated blood or human blood 5 which is ready for passing through a column 4 is sucked up using a pump 10 and is allowed to pass through the column 4. At this time, an inlet pressure measurement device 8 and an outlet pressure measurement device 9 are used to measure the respective pressures to thereby determine a pressure loss. Simulated blood or human blood 5 which is ready for passing through the column is kept in a constant temperature water bath 11 at a constant temperature of 37° C. In addition, a constant temperature water bath 11 is kept at constant temperature using a heater 12. For a circuit 7, a commercially available blood circuit can be used.

The loading density means a dry weight (g) of the material for blood purification in the form of a knitted fabric per unit volume ($cm^3$) of the material for blood purification in the form of a knitted fabric loaded in a container. For example, 1 g dry weight of the material for blood purification in the form of a knitted fabric loaded in a container having a volume of 1 $cm^3$ has a loading density of 1 $g/cm^3$.

The opening ratio means a ratio of the opening portions to the sum of the opening portions (3 in FIG. 1) and the non-opening portions (2 in FIG. 1) in the material for blood purification in the form of a knitted fabric, and is a value obtained by image processing. Specifically, the opening ratio is calculated using the following procedures.

1. The material for blood purification in the form of a knitted fabric is photographed using an optical microscope at a magnification ratio of 10×.

2. An image editing software (for example, "Photoshop Elements 14" available from Adobe Inc.) is launched, and the following operations are carried out in this order.

(1) A file of an image photographed using an optical microscope is opened.

(2) A part the opening ratio of which needs to be determined is cut out at 512 pixels×512 pixels (262144 pixels).

(3) Using Lighting for image adjustment, corrections are made on the opening portions and the non-opening portions that show the portions of the material for blood purification in the form of a knitted fabric in the image ('Lighten Shadow', and 'Midtone Contrast' in Shadow/Highlights are adjusted to 100% respectively; 'Contrast' in 'Brightness/Contrast' is adjusted to 100; and 'Brightness' is adjusted to 10).

(4) If parts of the opening portions and the portions of the material for blood purification in the form of a knitted fabric (non-opening portions) are uncorrected, the uncorrected parts of the opening portions and the uncorrected parts of the portions of the material for blood purification in the form of a knitted fabric are painted black and white respectively using the Brush tool in the drawing menu.

(5) The image is binarized by correcting the color tone in the filter into two-gradation. The value is corrected in comparison with the image yet to be corrected into two-gradation. The black portions and the white portions are made as the opening portions and the portions of the material for blood purification in the form of a knitted fabric (non-opening portions) respectively.

(6) The histogram in the window is opened, and the ratio of the black portions to the whole portions is regarded as an opening ratio (%).

The term "Blood purification" means a state in which at least one blood component has been removed by separation from blood by at least one operation of adsorption, dialysis, or inactivation using a material for blood purification.

The term "Blood components" refer to components constituting blood, and examples thereof include humoral factors in blood and cells in blood. The blood components to be removed by separation from blood by blood purification are not limited to particular ones. It is preferable that humoral factors in blood are removed, and it is more preferable that humoral factors in blood and cells in blood are simultaneously removed.

The mode of blood purification of blood components is not limited to a particular one, and in blood purification of humoral factors from blood, the humoral factors are preferably removed from blood by electrostatic interaction or hydrogen binding with the amide group(s) and amino group(s) in the water-insoluble carrier included in the material for blood purification and by hydrophobic interaction with the substrate. In addition, in blood purification of cells from blood, the cells are preferably removed by electrostatic interaction with the amino group(s) because cells in blood generally have negative electric charge.

The "Humoral factors in blood" means components contained in blood. Specific examples of humoral factors include: metals such as sodium, potassium, calcium, magnesium, manganese, iron, and cobalt, and ions thereof; phosphorus and ions thereof; proteins such as urea, $\beta$2-microglobulin, cytokines, IgE, and IgG; cells such as erythrocytes, lymphocytes, granulocytes, monocytes, and platelets; polysaccharides such as lipopolysaccharide (LPS); viruses such as influenza virus and HIV virus; and bacteria such as *Staphylococcus aureus*. Among these, metals having a structure that interacts with the amide group(s) and the amino group(s) and ions of the metals, phosphorus and ions thereof, proteins such as urea and cytokines, and polysaccharides are generally preferable as subjects of blood purification. Furthermore, cytokines are more preferable for the purpose of treating inflammatory diseases.

The term "Cells in blood" means cells contained in blood, and examples of cells include leukocyte components such as granulocytes, monocytes, neutrophils, and eosinophils; erythrocytes; and platelets. Leukocyte components are preferably removed for the purpose of treating inflammatory diseases. Among these, activated leukocyte-activated platelet complexes are preferably removed, and activated leukocytes and activated leukocyte-activated platelet complexes are particularly preferably removed.

The term "Activated leukocytes" means leukocytes that are caused by cytokines, LPS, and the like to release cytokines, active oxygen, or the like, and examples of activated leukocytes include activated granulocytes and activated monocytes. The degree of activation can be determined by measuring the amount of activated oxygen released by activated leukocytes or measuring the expression of surface antigens by flow cytometry and the like.

The term "Activated platelets" means platelets that are caused by cytokines, LPS, and the like to release cytokines, active oxygen, or the like.

The term "Activated leukocyte-activated platelet complexes" are not limited to particular ones as far as they are complexes wherein an activated leukocyte and an activated platelet are bound to each other, and examples thereof include activated granulocyte-activated platelet complexes and activated monocyte-activated platelet complexes. For treating patients with an inflammatory disease, it is considered to be necessary to remove activated leukocyte-activated platelet complexes that are considered to be directly related to the pathology through phagocytosis into self-tissues and release of cytokines.

The "Cytokines" means a group of proteins which, through a stimulus such as infection or trauma, are produced from various cells such as immunocompetent cells, released extracellularly, and allowed to act, and examples of cytokines include interferon-$\alpha$, interferon-$\beta$, interferon-$\gamma$, interleukin-1 to interleukin-15, tumor necrosis factor-$\alpha$, tumor necrosis factor-$\beta$, high-mobility group box-1, erythropoietin, and monocyte chemotactic factors.

The material for blood purification according to the present embodiment is preferably used for removal of cytokines, more preferably used for removal of interleukin-1$\beta$, interleukin-6, interleukin-8, or high-mobility group box-1. In addition, the material for blood purification according to the present embodiment is more preferably used for removal of cytokines and activated leukocyte-activated platelet complexes, still more preferably used for removal of cytokines, activated leukocytes, and activated leukocyte-activated platelet complexes, still more preferably used for removal of cytokines selected from the group consisting of interleukin-1 interleukin-6, interleukin-8, and high-mobility group box-1 and for removal of activated leukocyte and activated leukocyte-activated platelet complexes.

The term "inflammatory disease" collectively refers to a disease that initiates inflammatory reaction in the body, and an inflammatory disease which can be treated is not limited to a particular one. Examples of inflammatory diseases include systemic lupus erythematosus, malignant rheumatoid arthritis, multiple sclerosis, ulcerative colitis, crohn's disease, drug-induced hepatitis, alcoholic hepatitis, hepatitis A, hepatitis B, hepatitis C, hepatitis D, hepatitis E, sepses (for example, sepsis derived from gram-negative bacteria, sepsis derived from gram-positive bacteria, culture-negative sepsis, a fungal sepsis), influenza, acute respiratory distress syndrome (ARDS), acute lung injury (ALI), pancreatititis, idiopathic pulmonary fibrosis (IPF), inflammatory enteritis (for example, ulcerative colitis and crohn's disease), transfusion of a blood preparation, organ transplantation, reperfusion damage caused by organ transplantation, cholecystitis, cholangitis, or newborn blood group incompatibility, and the like. Among inflammatory diseases, preferable subjects are drug-induced hepatitis, alcoholic hepatitis, hepatitis A, hepatitis B, hepatitis C, hepatitis D, hepatitis E, sepses (for example, sepsis derived from gram-negative bacteria, sepsis derived from gram-positive bacteria, culture-negative sepsis, and fungal sepsis), influenza, acute respiratory distress syndrome (ARDS), acute lung injury (ALI), pancreatititis, and idiopathic interstitial pneumonia (IPF), which cause causative agents to be released in blood and can particularly be expected to be treated effectively with blood purification; and more preferable subjects in particular are sepses (for example, sepsis derived from gram-negative bacteria, sepsis derived from gram-positive bacteria, culture-negative sepsis, and fungal sepsis), influenza, acute respiratory distress syndrome (ARDS), acute lung injury (ALI), idiopathic pulmonary fibrosis (IPF), which are difficult to treat with pharmaceuticals alone and in which both cytokines and activated leukocyte-activated platelets are involved.

The term "Adsorption" means a state in which humoral factors in blood are adherent to the material for blood purification and cannot be easily released from the material. Specifically, the adsorption refers to a state in which humoral factors in blood are adherent to the material for blood purification via an intermolecular force such as electrostatic interaction, hydrophobic interaction, hydrogen binding, and van der Waals force, although the mode of adsorption is not limited thereto.

The material for blood purification according to the present invention is preferably used as a carrier that is loaded into an apparatus for blood purification. In cases where an apparatus for blood purification using the material for blood purification according to the present invention is used for blood purification therapy as a column for extracorporeal circulation, blood delivered out of the body may be allowed to directly pass through the column, or the column may be used in combination with a blood plasma separation membrane and the like.

The apparatus for blood purification needs only to be in the shape of a container having an inlet and an outlet for blood. Examples of the apparatus include a container in the shape of a cylindrical pole or a container in the shape of a rectangular column such as a triangle pole, a square pole, a hexagonal pole, or an octagonal pole. Preferable containers are a container in which a carrier for adsorption of blood components can be loaded in the form of a laminate, a container in which a carrier for adsorption of blood components can be loaded in the form of a cylindrical roll, and a cylindrical container such that blood is allowed to flow into the container from the periphery of the cylinder and go out of the container.

The material for blood purification can be produced using a method, for example, but not limited to, the following production method.

When a water-insoluble material comprising a polymer and a reinforcing material comprising a polymer are mixed, a material mixture of the substrate and the reinforcing material is obtained in such a manner that the substrate and the reinforcing material are heated to a glass transition temperature or higher, kneaded (for example, melt-kneaded using a biaxial kneading extruder), and adhered to each other (for example, by contact bonding with a press machine or by melt spinning to afford a sea-island structure), or in such a manner that the substrate is dissolved in a good solvent, the reinforcing material is coated with the substrate solution, and only the solvent is evaporated. Then, binding the substrate and the ligand that are included in the material mixture of the substrate and the reinforcing material, which is obtained by the above-mentioned operation, can achieve a mixture of the water-insoluble material comprising a polymer and the reinforcing material comprising a polymer.

As for the production of a water-insoluble material in which a ligand having an amide group(s) and an amino group(s) is bound to a substrate, for example, a carbamoyl chloride-bonded substrate is produced by adding a substrate to a solution of a Lewis acid (for example, aluminium (III) chloride) and carbamoyl chloride having a halogenated alkyl group (for example, N,N-Bis(2-chloroethyl)carbamoyl Chloride) dissolved in a non-polar solvent (for example, dichloromethane) and by stirring the resultant. Then, the reacted substrate is taken out and added to a solution of an amine compound (for example, tetraethylenepentaamine) dissolved in dimethyl sulfoxide, whereby the water-insoluble material can be produced.

The substrate to be used can be any commercially available one. In this regard, the substrate is preferably one formed into fiber, more preferably a fiber containing polystyrene or a derivative thereof. Polystyrene or a derivative thereof can be produced by a known method or a similar method. The reinforcing material to be used can be any commercially available one, and is preferably polyethylene or polypropylene.

Among the materials for blood purification represented by the above-mentioned Formula (II), an amidemethylated-aminated-phenylated form (II-a) in which A is a urea bond or an amide bond can be produced, for example, by reaction between an amidemethylated-aminated form represented by the above-mentioned Formula (I) and a benzene derivative (III), as shown in Scheme 1.

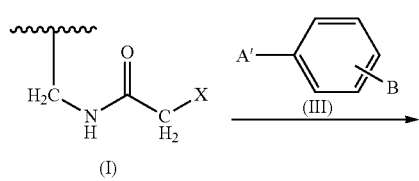

Scheme 1

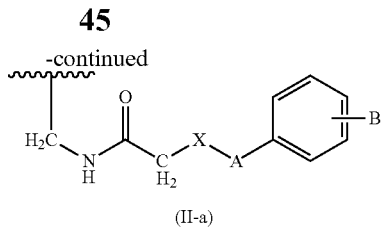

(II-a)

(wherein, when A is a urea bond, A' represents an isocyanate group; when A is an amide bond, A' represents an acid chloride group; and the other symbols are synonymous with the above-mentioned definitions.)

The benzene derivative (III) to be used for reaction can be any commercially available one.

Examples of reaction solvents include N,N-dimethyl formamide, diethyl ether, dioxane, tetrahydrofuran, and dimethyl sulfoxide, and N,N-dimethyl formamide or dimethyl sulfoxide is preferable.

The reaction temperature is preferably 10 to 90° C., more preferably 30 to 60° C.

The reaction time is preferably 1 to 24 hours.

An amidemethylated-aminated form represented by the above-mentioned Formula (I) can be produced, for example, by reaction between a halogenated amidemethylated form (V) and an amine derivative (IV), as shown in Scheme 2.

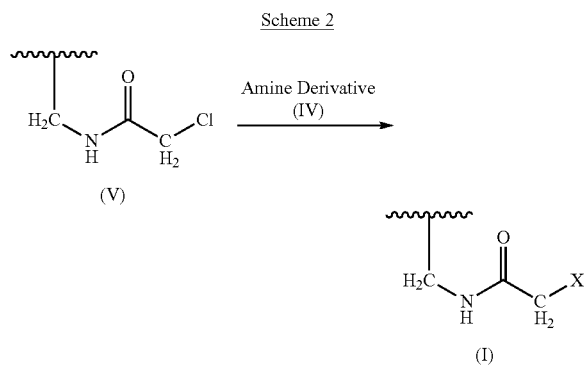

Scheme 2

(wherein X and the wavy line are synonymous with the above-mentioned definitions.)

The amine derivative (IV) to be used for reaction can be any commercially available one.

Examples of reaction solvents include N,N-dimethyl formamide, diethyl ether, dioxane, tetrahydrofuran, and dimethyl sulfoxide, and dimethyl sulfoxide is preferable.

Examples of catalysts include organic bases such as triethylamine or 1,4-diazabicyclo[2.2.2]octane; and inorganic bases such as sodium hydroxide. Organic bases such as triethylamine are preferable.

The concentration of a catalyst in the reaction solution is preferably 50 to 1000 mM, more preferably 300 to 700 mM.

The amount of the reaction liquid is preferably 5 to 1000 mL, more preferably 50 to 500 mL, with respect to 1 g of the halogenated amidemethylated form (V).

The reaction temperature is preferably 15 to 80° C., more preferably 40 to 60° C.

The reaction time is preferably 30 minutes to 24 hours, preferably 1 to 8 hours.

The halogenated amidemethylated form (V) can be produced, for example, by introducing N-methylol-α-chloroacetamide (VI) into a substrate (VII), as shown in Scheme 3.

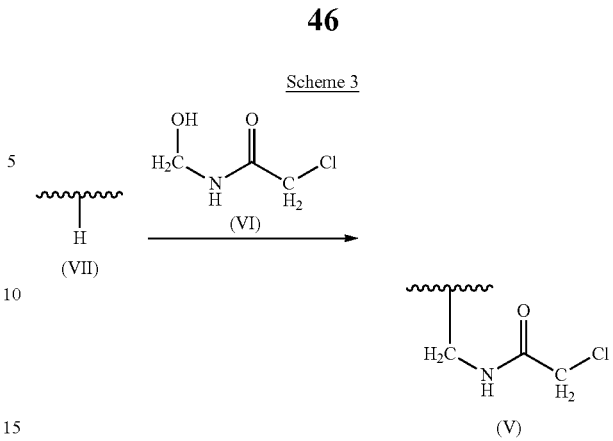

Scheme 3

(wherein the wavy line is synonymous with the above-mentioned definition.)

The substrate (VII) and N-methylol-α-chloroacetamide (VI) can each be any commercially available one. In this regard, the substrate (VII) is preferably one formed into fiber, more preferably a fiber containing polystyrene or a derivative thereof.

Examples of reaction solvents include nitrobenzene, nitropropane, chlorobenzene, toluene, and xylene. Nitrobenzene or nitropropane is preferable.

Examples of catalysts include Lewis acids such as sulfuric acid, hydrochloric acid, nitric acid, halogenated aluminum (III) (for example, aluminium chloride (III)), and halogenated iron (III) (for example, ferric chloride (III)). Sulfuric acid or ferric chloride (III) is preferable.

The concentration of a catalyst in the reaction solution is preferably 5 to 80 wt %, more preferably 30 to 70 wt %.

The reaction temperature is preferably 0 to 90° C., more preferably 5 to 40° C.

The reaction time is preferably 1 minute to 120 hours, more preferably 5 minutes to 24 hours.

In addition, a solution in which paraformaldehyde is dissolved may be added to the reaction solution before the substrate (VII) is added to the reaction solution. The solvent in which paraformaldehyde is dissolved is not limited to any one, and preferably has the same solvent composition as that of the reaction solution. The time from addition of a paraformaldehyde solution to addition of the substrate (VII) is preferably 1 to 30 minutes, more preferably 1 to 5 minutes.

The amino group content of the water-insoluble material included in the material for blood purification can be determined in a step wherein only the water-insoluble material is taken out by allowing the reinforcing material contained in the material for blood purification to be dissolved in a solvent in which only the reinforcing material can be dissolved, the water-insoluble material is dried, the dry weight is measured, the amino group in the water-insoluble material is ion-exchanged with hydrochloric acid, and the resulting material is subjected to back titration with a sodium hydroxide aqueous solution. The solid is measured for weight and then dried by heating at 80° C. at atmospheric pressure for 24 hours. The solid is considered to be in a dry state when the remaining solid undergoes a weight reduction of 1 wt % or less compared with the weight of the solid before drying. When the reduction in weight is more than 1 wt %, the step wherein the solid is dried by heating at 80° C. at atmospheric pressure for 24 hours can be repeated until the reduction in weight becomes less than 1 wt %, so that the solid can be in a dry state. The material for blood purification not containing a reinforcing material does not require an operation to dissolve a reinforcing material in a solvent.

The amide group content of the water-insoluble material included in the material for blood purification can be determined in a step wherein only the water-insoluble material is taken out by allowing the reinforcing material contained in the material for blood purification to be dissolved in a solvent in which only the reinforcing material can be dissolved, the water-insoluble material is dried, the dry weight is measured, the amino group(s) in the water-insoluble material is heated in hydrochloric acid to be hydrolyzed, the generated amino group is ion-exchanged with hydrochloric acid, and the resulting material is subjected to back titration with a sodium hydroxide aqueous solution. The material for blood purification not containing reinforcing material does not require an operation to dissolve a reinforcing material in a solvent.

The phenyl group content of the water-insoluble material included in the material for blood purification can be determined in a step wherein only the water-insoluble material is taken out by allowing the reinforcing material contained in the material for blood purification to be dissolved in a solvent in which only the reinforcing material can be dissolved, the water-insoluble material is dried, the dry weight is measured, the amino group in the water-insoluble material is heated in hydrochloric acid to be hydrolyzed, the amount of the phenyl group-derived compound contained in the hydrochloric acid is measured by $^1$HNMR, and the concentration of the compound in the hydrochloric acid is measured using a calibration curve made using an internal standard. The material for blood purification not containing a reinforcing material does not require an operation to dissolve a reinforcing material in a solvent.

In addition, the present invention is characterized by providing an apparatus for blood purification including the above-mentioned material for blood purification.

The term "apparatus for blood purification" refers to a product by which blood is circulated to and from the outside of the body and in which at least a part of the product includes a medical material intended to remove waste products and harmful substances from the blood. Examples of the apparatus include a module for an artificial kidney, an extracorporeal circulation column, and the like.

Furthermore, the apparatus for blood purification including the material for blood purification can be suitably used in inflammatory disease treatment applications. When the apparatus for blood purification is used for inflammatory disease treatment, an extracorporeal circulation method is preferable in which the apparatus for blood purification including the material for blood purification is connected with a patient via a blood circuit, and the bodily fluid taken out of the patient is allowed to pass through an extracorporeal circulation column according to the present invention, and returned to the patient. The processing time of the bodily fluid and the like is preferably continuous, more preferably 4 hours or more, still more preferably 24 hours or more, in the light of inhibiting inflammation from being further induced by blood components.

The apparatus for blood purification including the material for blood purification may be used together with another bodily fluid processing method or another medical apparatus. Examples of other bodily fluid processing methods and medical apparatuses include plasma exchange, peritoneal dialysis, plasma separators, hemofilters, artificial hearts and lungs, and ECMO.

Examples of methods of evaluating the blood purification performance of the material for blood purification include a method in which cytokines are dissolved in fetal bovine serum (hereinafter referred to as FBS), the material for blood purification is impregnated with the FBS, the amount of reduction in the concentration of cytokines in the FBS is evaluated after the impregnation, and the adsorption rate is calculated. As described in Non Patent Document 1 and 2, a cytokine is a substance that is preferably removed from blood in order to improve pathology. Therefore, the blood purification performance can be judged to be higher as the amount of reduction in the concentration becomes larger by the impregnation. Examples of cytokines include interleukin-1β, interleukin-6, interleukin-8, high-mobility group protein-1, and tumor necrosis factor-β. Interleukin-6 and interleukin-8 are more preferable in view of being typical biomarkers in practice of treatment of inflammatory diseases.

In addition, examples of methods of evaluating the blood purification performance of the material for blood purification include a method in which a removal rate of each of an activated granulocyte, an activated monocyte, an activated granulocyte-activated platelet complex, and an activated monocyte-activated platelet complex is evaluated. Examples of methods of calculating a removal rate of each of an activated granulocyte, an activated monocyte, an activated granulocyte-activated platelet complex, and an activated monocyte-activated platelet complex include a method in which a container having an inlet and an outlet is loaded with the material for blood purification, a liquid containing an activated granulocyte, an activated monocyte, an activated granulocyte-activated platelet complex, and an activated monocyte-activated platelet complex is allowed to pass through the container, and the removal rate is calculated from a change between the concentration at the inlet and that at the outlet.

A removal rate of 6% or more can be judged to be a significant removal in that an activated granulocyte, an activated monocyte, an activated granulocyte-activated platelet complex, and an activated monocyte-activated platelet complex are cells and imply the measurement dispersion of the removal rate.

The concentration of an activated leukocyte-activated platelet complex can be measured, for example, in such a manner that an activation detection reagent that is specifically bound to an activated platelet (an activated platelet binding reagent) and an activation detection reagent that is specifically bound to an activated leukocyte (an activated leukocyte detection reagent/an activated granulocyte detection reagent/an activated monocyte detection reagent) are allowed to react with the fraction of leukocyte derived from peripheral blood, and the fraction of the blood corpuscle bound to both reagents is measured.

An activated platelet detection reagent is not bound to a deactivated leukocyte nor an activated leukocyte and has the binding ability with an activated platelet, and the activated platelet is detected using CD62P (Anti-human CD62P (P-Selectin) Antibody Data Sheet, BioLegend.) known as a cell surface marker specific to an activated platelet. An activated leukocyte detection reagent is not bound to a deactivated platelet nor an activated leukocyte and has the binding ability with an activated leukocyte, and examples of the detection reagent include an antibody specific to a desired leukocyte component and an antibody against a cell surface marker common to a desired leukocyte component. As a detection reagent for an activated granulocyte and an activated monocyte, for example, an anti-CD11b antibody can be used. Among these, using an activated anti-CD11b antibody that can specifically detect an activated conformation makes it possible to specifically detect an activated granulocyte and an activated monocyte (Anti-human CD11b (activated) Antibody Data Sheet, BioLegend.). An anti-CD45 antibody can be used to detect leukocytes, an anti-CD66b antibody in a CD45 positive cell can be used to detect granulocytes, and an anti-CD14 antibody in a CD45 positive cell can be used to detect monocytes. To detect lymphocytes, an anti-CD4 antibody and an anti-CD8 antibody can be used, and it is also possible that a cell population obtained by subtracting CD66b positive cells and CD14 positive cells from CD45 positive cells is regarded as lymphocytes.

The above-mentioned detection reagents preferably have an index imparted thereto for verifying the binding. Any index can be selected in accordance with an adopted detection method. A flow cytometer is used for measurement from an easy operation or quantitativeness point of view, in which case, a detection reagent is fluorescently-labeled. The fluorescent label is not limited to a particular one, and, for example, labeling with FITC (fluorescein isothiocyanate) or PE (R-phycoerythrin) can be adopted. The activated leukocyte detection reagent and the activated platelet detection reagent are labelled with different fluorescent substances. These labelled detection reagents can be produced by a conventional method, and is also commercially available.

The reaction between a leukocyte fraction and a detection reagent is suitably set in accordance with the detection reagent adopted. When the detection reagent is an antibody, the reagent has only to be subjected to a usual immunoreaction. The activated leukocyte-activated platelet complex and the detection reagent reaction liquid are not limited to particular ones, and, if desired, may contain sodium azide or formaldehyde in an amount effective in inhibiting the activation of cell components during detection reaction. The reaction temperature is not limited particularly, and is preferably about 4° C. with a view to inhibiting the activation of cell components.

EXAMPLES

The material for blood purification according to the present invention will now be specifically described with reference to Examples, but the present invention is not to be limited to these examples.

In Examples, wt % means % by weight. M represents mol/L, and mM represents mmol/L. Unless otherwise specified, the weight of a knitted fabric, a material for blood purification, or a water-insoluble material is a dry weight. A total fineness refers to a weight (gram) per 10000 m of fiber, and is notated as dtex. A pH measurement in acid-base titration was carried out by immersing the electrode of a benchtop pH meter, F-74BW (with a standard ToupH electrode, 9615S-10D) made by Horiba, Ltd. in a 25° C. solution. Before the measurement, calibration was carried out using a neutral phosphate standard solution (a monopotassium phosphate aqueous solution (3.40 g/L), made by Wako Pure Chemical Industries, Ltd.) and a phthalate standard solution (a potassium hydrogen phthalate aqueous solution (10.21 g/L), made by Wako Pure Chemical Industries, Ltd.). An ultraviolet and visible spectrophotometer (UV-1280) made by Shimadzu Corporation was used to measure absorbance at room temperature. Before the measurement of absorbance, a blank measurement was performed preliminarily, and the peaks on the background were subtracted. A total reflection infrared absorption spectrum was measured using a Nicolet iS5 FT-IR (with an iD5 Diamond ATR accessory) made by Thermo Fisher Scientific Inc. Before the measurement of infrared spectroscopy, a blank measurement was performed preliminarily, and the peaks on the background were subtracted.

(Preparation of Fiber A)

A 16-island sea-island composite fiber described in Description of Patent Document 1 (JP 4591974 B2) (hereinafter referred to as Fiber A) was obtained using the following components.
Island component: polypropylene
Sea component (weight ratio): polystyrene:polypropylene=92:8
Composite ratio (weight ratio): island component:sea component=50:50
Total fineness: 160 dtex
Single yarn diameter: 20 μm (Preparation of Fiber B)

A 32-island sea-island composite fiber described in Description of Patent Document 3 (JP 5293599 B2), wherein the islands were further core-sheath composites, (hereinafter referred to as Fiber B) was obtained using the following components under yarn-making conditions including a spinning rate of 800 m/minute.
Core component of island: polypropylene
Sheath component of island: polystyrene and polypropylene kneaded at a ratio of 90 wt % and 10 wt % respectively
Sea component: "copolyester whose main repeating unit is an ethylene terephthalate unit and which contains 3 wt % of 5-sodium sulfoisophthalic acid as a copolymerization component" (hereinafter referred to as PETIFA)
Composite ratio (weight ratio): core component of island: sheath component of island:sea component=41.5:33.5:25
Total fineness: 200 dtex (Preparation of Knitted Fabric A)

As described in Description of Patent Document 1, Fiber A was used to prepare a circularly knitted fabric A having a dry weight of 0.0081 g/cm$^2$ and a bulk density of 0.37 g/cm$^3$ (hereinafter referred to as Knitted Fabric A).

(Preparation of Knitted Fabric B)

Fiber B was made into a circular knitting using a circular knitting machine (machine name: a circular knitting machine, MR-1, made by Maruzen Sangyo Co., Ltd.), and further impregnated with a 3 wt % sodium hydroxide aqueous solution at 95° C. for eight hours to hydrolyze PETIFA of the sea component. Next, the knitting was washed with water until the knitting was neutral. Subsequently, the knitting was dried to prepare a circularly knitted fabric B whose core-sheath fiber had a single yarn diameter of 4.5 μm and which had a dry weight of 0.0046 g/cm$^2$ and a bulk density of 0.4 g/cm$^3$ (hereinafter referred to as Knitted Fabric B).

(Preparation of Knitted Fabric C)

Fiber A was used and the density adjustment scale of a circular knitting machine (machine name: a circular knitting machine, MR-1, made by Maruzen Sangyo Co., Ltd.) was adjusted to prepare a circularly knitted fabric C having a weight per cm$^2$ of 0.0210 g/cm$^2$ and a bulk density of 0.51 g/cm$^3$ (hereinafter referred to as Knitted Fabric C).

(Preparation of Knitted Fabric D)

Fiber A was used and the density adjustment scale of a circular knitting machine (machine name: a circular knitting machine, MR-1, made by Maruzen Sangyo Co., Ltd.) was adjusted to prepare a circularly knitted fabric D having a weight per cm$^2$ of 0.0153 g/cm$^2$ and a bulk density of 0.42 g/cm$^3$ (hereinafter referred to as Knitted Fabric D).

(Preparation of Knitted Fabric E)

Fiber A was used and the density adjustment scale of a circular knitting machine (machine name: a circular knitting machine, MR-1, made by Maruzen Sangyo Co., Ltd.) was adjusted to prepare a circularly knitted fabric E having a weight per cm² of 0.0063 g/cm² and a bulk density of 0.28 g/cm³ (hereinafter referred to as Knitted Fabric E).

(Preparation of Knitted Fabric E)

Fiber A was used and the density adjustment scale of a circular knitting machine (machine name: a circular knitting machine, MR-1, made by Maruzen Sangyo Co., Ltd.) was adjusted to prepare a circularly knitted fabric F having a weight per cm² of 0.0039 g/cm² and a bulk density of 0.22 g/cm³ (hereinafter referred to as Knitted Fabric F).

(Preparation of Material 1 for Blood Purification)

As described in the Description of Patent Document 1 (JP 4591974 B2), 50 g of Knitted Fabric A was immersed in a solution mixture of 50 g of N-methylol-α-chloroacetamide (hereinafter referred to as NMCA), 400 g of nitrobenzene, 400 g of 98 wt % sulfuric acid, and 0.85 g of paraformaldehyde (hereinafter referred to as PFA), and the resultant was allowed to react at 4° C. for one hour. The reacted fiber was immersed in 5 L of 0° C. ice water to terminate the reaction, and then washed with water. The nitrobenzene attached to the fiber was removed by extraction with methanol to obtain a chloroacetamidemethylated cross-linked polystyrene knitted fabric 1 (hereinafter referred to as AMPSt Knitted Fabric 1).

Tetraethylenepentamine (hereinafter referred to as TEPA) in an amount of 1.5 g was dissolved in 500 mL of dimethyl sulfoxide (hereinafter referred to as DMSO). To the resulting solution, 20 g of AMP St Knitted Fabric 1 was added with stirring, and the resultant was allowed to react at 25° C. for six hours. The reacted AMPSt Knitted Fabric 1 was washed with 500 mL of DMSO on a glass filter. After the washing, 3.0 g of AMPSt Knitted Fabric 1 was added to a solution of 1.0 g of p-chlorophenyl isocyanate dissolved in 150 mL of DMSO, and the resultant was allowed to react at 25° C. for one hour. Thereafter, the fiber was washed with DMSO and distilled water, 60 mL each, on a glass filter, and further washed with distilled water and physiological saline, 3 L each, to obtain a knitted fabric 1 which was a material for blood purification (hereinafter referred to as Material 1 for Blood Purification). The existence or absence of the binding of a ligand having an amide group(s) and an amino group(s) to Material 1 for Blood Purification was confirmed in accordance with whether there were any amide group-derived peak (1650 cm$^{-1}$) and any amino group-derived peak (1540 cm$^{-1}$) appearing on a total reflection infrared absorption spectrum. The measurement was performed in such a manner that Material 1 for Blood Purification was left to stand in a dryer at 60° C. for four hours to be dried and that the dried Material 1 was pressed against the prism of an infrared spectrometer.

(Measurement of Amino Group Content of Water-Insoluble Material 1 Included in Material 1 for Blood Purification)

The amino group content of Water-insoluble Material 1 included in Material 1 for Blood Purification was determined by acid-base back titration of the amino group amount of Water-insoluble Material 1. To a 200 mL egg-plant shaped flask, 5.0 g of Material 1 for Blood Purification and 100 mL of toluene were added, and the resultant was refluxed at 150° C. for 24 hours to thereby remove polypropylene that had been added as a reinforcing material. After the reflux, the solution was promptly added to 2 L of toluene heated to 100° C., and washed. Only the insoluble component was collected by filtration through a paper filter, washed with methanol, and left to stand in a dryer at 80° C. for 48 hours to obtain Water-insoluble Material 1. Then, to a polypropylene container, 1.0 g of Water-insoluble Material 1 and 50 mL of a 6 M sodium hydroxide aqueous solution were added, the resultant was stirred for 30 minutes, and Water-insoluble Material 1 was collected by filtration using a paper filter. Then, to 50 mL of ion-exchanged water, the filtrated Water-insoluble Material 1 was added, and the resultant was stirred for 30 minutes and filtrated using a paper filter. The Water-insoluble Material 1 was added to ion-exchanged water until the ion-exchanged water with the Water-insoluble Material 1 added thereto had a pH of 7, and the resultant was filtrated, which addition and filtration were repeated to obtain Water-insoluble Material 1 that was desalted. The desalted Water-insoluble Material 1 was left to stand at 80° C. under normal pressure conditions for 48 hours, 1.0 g of the Water-insoluble Material 1 and 30 mL of 0.1 M hydrochloric acid were added to a polypropylene container, and the resultant was stirred for ten minutes. After the stirring, 5 mL of the solution alone was pulled out and transferred into a polypropylene container. Then, to the obtained solution, 0.1 mL of a 0.1 M sodium hydroxide aqueous solution was added dropwise. After the dropwide addition, the resulting mixture was stirred for ten minutes, and the pH of the solution was measured. The same operation of dropwise addition, ten-minute stirring, and pH measurement was repeated 100 times. The amount of the sodium hydroxide aqueous solution added dropwise until the pH of the solution exceeded 8.5 was regarded as a titer per 1 g. The content of the amino group(s) per 1 g dry weight of Water-insoluble Material 1 was calculated using the titer per 1 g and the following Equation 1.

Content of Amino Group per 1 g Dry Weight of Water-insoluble Material (mmol/g)={Added 0.1 M Hydrochloric Acid Liquid Amount (30 mL)/Pulled-out Hydrochloric Acid Liquid Amount (5 mL)}×Titer per 1 g (mL)×Sodium Hydroxide Aqueous Solution Concentration (0.1 M)  Equation 1

(Measurement of Amide Group Content of Water-Insoluble Material 1 Included in Material 1 for Blood Purification)

The amide group content of Water-insoluble Material 1 included in Material 1 for Blood Purification was determined by hydrolyzing the amide group in Water-insoluble Material 1 to thereby generate the amino group and by measuring the amount of the generated amino group by acid-base back titration. Water-insoluble Material 1 was obtained from Material 1 for Blood Purification in the same manner as in Measurement of Amino Group Content of Water-insoluble Material 1. Then, 1.0 g of the Water-insoluble Material 1 and 100 mL of 6M hydrochloric acid were added to a 200 mL egg-plant shaped flask and refluxed at 130° C. for 24 hours. After the reflux, Water-insoluble Material 1 was collected by filtration using a paper filter to obtain Water-insoluble Material 1 that was decomposed. Then, to a polypropylene container, all the amount of the resulting decomposed Water-insoluble Material 1 and 50 mL of a 6 M sodium hydroxide aqueous solution were added, the resultant was stirred for 30 minutes, and filtrated using a paper filter. Then, to 50 mL of ion-exchanged water, the filtrated decomposed Water-insoluble Material 1 was added, and the resultant was stirred for 30 minutes and filtrated using a paper filter. The Water-insoluble Material 1 was added to ion-exchanged water until the ion-exchanged water with the Water-insoluble Material 1 added thereto had a pH of 7, and the resultant was filtrated, which addition and filtration were repeated, and the Water-insoluble Material 1 was left to stand at 80° C. under normal pressure conditions for 48 hours. Then, all the amount of the Water-insoluble Material 1 and 60 mL of 0.1 M hydrochloric acid were added to a polypropylene container, followed by stirring for ten minutes. After the stirring, 5 mL of the solution alone was pulled out and transferred into a polypropylene container. Then, to the obtained solution, 0.1 mL of a 0.1 M sodium hydroxide aqueous solution was added dropwise. After the dropwide addition, the resulting mixture was stirred for ten minutes, and the pH of the solution was measured. The same operation of dropwise addition, ten-minute stirring, and pH measurement was repeated 100 times. The amount of the sodium hydroxide aqueous solution added dropwise until the pH of the solution exceeded 8.5 was regarded as a titer per 1 g. The content of the amide group(s) per 1 g dry weight of Water-insoluble Material 1 was calculated using the titer per 1 g and the following Equation 2.

Content of Amide Group per 1 g Dry Weight of Water-insoluble Material (mmol/g)={Added 0.1 M Hydrochloric Acid Liquid Amount (60 mL)/Pulled-out Hydrochloric Acid Liquid Amount (5 mL)}×Titer per 1 g (mL)×Sodium Hydroxide Aqueous Solution Concentration (0.1 M)   Equation 2

(Preparation of Material 2 for Blood Purification)

As described in the Description of Patent Document 2 (JP 5824873 B2), 50 g of Knitted Fabric A was reacted with a solution mixture of 50 g of NMCA, 400 g of nitrobenzene, 400 g of 98 wt % sulfuric acid, and 0.85 g of PFA at 20° C. for one hour.

Then, the fiber was washed with nitrobenzene and put into water to thereby terminate the reaction. Thereafter, the fiber was washed again with hot water to thereby obtain a chloroacetamidemethylated cross-linked polystyrene knitted fabric 2 (hereinafter referred to as AMPSt Knitted Fabric 2).

TEPA in an amount of 0.9 g was dissolved in 50 ml of dimethyl sulfoxide, and to this solution, 1 g of AMPSt Knitted Fabric 2 was added with stirring. The reaction was carried out at 25° C. for six hours. Then, AMPSt Knitted Fabric 2 was washed on a glass filter using 200 ml of N,N-dimethylformamide (hereinafter referred to as DMF), and added to a solution of 1 g of p-chlorophenyl isocyanate dissolved in 50 ml of DMF. The resultant was allowed to react at 25° C. for one hour. Thereafter, the resultant was washed with 200 ml of DMF and 200 ml of distilled water on a glass filter to obtain Knitted Fabric 2 which was a material for blood purification (hereinafter referred to as Material 2 for Blood Purification).

(Measurement of Amino Group Content of Water-Insoluble Material 2 Included in Material 2 for Blood Purification)

The same operation as for Material 1 for Blood Purification was carried out to measure the amino group content of Water-insoluble Material 2 included in Material 2 for Blood Purification. The results are shown in Table 5.

(Measurement of Amide Group Content of Water-Insoluble Material 2 Included in Material 2 for Blood Purification)

The same operation as for Material 1 for Blood Purification was carried out to measure the amide group content of Water-insoluble Material 2 included in Material 2 for Blood Purification. The results are shown in Table 5.

(Preparation of Material 3 for Blood Purification)

NMCA in an amount of 2.3 g was added to a solution mixture of 31 g of nitrobenzene and 31 g of 98 wt % sulfuric acid, and the resulting mixture was stirred at 10° C. until the NMCA was dissolved in the solution, to obtain an NMCA solution. Then, 0.2 g of PFA was added to 2.0 g of nitrobenzene and 2.0 g of 98 wt % sulfuric acid, and the resulting mixture was stirred at 20° C. until the PFA was dissolved in the solution, to obtain a PFA solution. The PFA solution in an amount of 4.2 g was cooled to 5° C. and mixed with 64.3 g of the NMCA solution, the resulting mixture was stirred for five minutes, 1 g of Knitted Fabric B was added to the mixture to be impregnated with the mixture for two hours. The impregnated Knitted Fabric B was immersed in 200 mL of 0° C. nitrobenzene to thereby terminate the reaction, and the nitrobenzene attached to the Fabric was removed by extraction with methanol.

TEPA in an amount of 0.16 g and triethylamine in an amount of 2.1 g were dissolved in 51 g of DMSO, and to this solution, the Knitted Fabric B obtained after the removal by extraction with methanol was added as it was. The Fabric was impregnated with the solution at 40° C. for three hours. The Knitted Fabric was collected on a glass filter by filtration, washed with 500 mL of DMSO, 3 L of distilled water, and physiological saline to obtain Knitted Fabric 3 which was a material for blood purification (hereinafter referred to as Material 3 for Blood Purification).

(Measurement of Amino Group Content of Water-Insoluble Material 3 Included in Material 3 for Blood Purification)

The same operation as for Material 1 for Blood Purification was carried out to measure the amino group content of Water-insoluble Material 3 included in Material 3 for Blood Purification. The results are shown in Table 5.

(Measurement of Amide Group Content of Water-Insoluble Material 3 Included in Material 3 for Blood Purification)

The same operation as for Material 1 for Blood Purification was carried out to measure the amide group content of Water-insoluble Material 3 included in Material 3 for Blood Purification. The results are shown in Table 5.

(Preparation of Material 4 for Blood Purification)

Knitted Fabric 4 which was a material for blood purification (hereinafter referred to as Material 4 for Blood Purification) was obtained by carrying out the same operation as for Material 3 for Blood Purification except that the added amount of TEPA was changed to 0.25 g.

(Measurement of Amino Group Content of Water-Insoluble Material 4 Included in Material 4 for Blood Purification)

The same operation as for Material 1 for Blood Purification was carried out to measure the amino group content of Water-insoluble Material 4 included in Material 4 for Blood Purification. The results are shown in Table 5.

(Measurement of Amide Group Content of Water-Insoluble Material 4 Included in Material 4 for Blood Purification)

The same operation as for Material 1 for Blood Purification was carried out to measure the amide group content of Water-insoluble Material 4 included in Material 4 for Blood Purification. The results are shown in Table 5.

(Preparation of Material 5 for Blood Purification)

Knitted Fabric 5 which was a material for blood purification (hereinafter referred to as Material 5 for Blood Purification) was obtained by carrying out the same operation as for Material 3 for Blood Purification except that the added amount of TEPA was changed to 0.82 g.

(Measurement of Amino Group Content of Water-Insoluble Material 5 Included in Material 5 for Blood Purification)

The same operation as for Material 1 for Blood Purification was carried out to measure the amino group content of Water-insoluble Material 5 included in Material 5 for Blood Purification. The results are shown in Table 5.

(Measurement of Amide Group Content of Water-Insoluble Material 5 Included in Material 5 for Blood Purification)

The same operation as for Material 1 for Blood Purification was carried out to measure the amide group content of Water-insoluble Material 5 included in Material 5 for Blood Purification. The results are shown in Table 5.

(Preparation of Material 6 for Blood Purification)

Knitted Fabric 6 which was a material for blood purification (hereinafter referred to as Material 6 for Blood Purification) was obtained by carrying out the same operation as for Material 3 for Blood Purification except that the added amount of TEPA was changed to 3.28 g.

(Measurement of Amino Group Content of Water-Insoluble Material 6 Included in Material 6 for Blood Purification)

The same operation as for Material 1 for Blood Purification was carried out to measure the amino group content of Water-insoluble Material 6 included in Material 6 for Blood Purification. The results are shown in Table 5.

(Measurement of Amide Group Content of Water-Insoluble Material 6 Included in Material 6 for Blood Purification)

The same operation as for Material 1 for Blood Purification was carried out to measure the amide group content of Water-insoluble Material 6 included in Material 6 for Blood Purification. The results are shown in Table 5.

(Preparation of Material 7 for Blood Purification)

Knitted Fabric 7 which was a material for blood purification (hereinafter referred to as Material 7 for Blood Purification) was obtained by carrying out the same operation as for Material 3 for Blood Purification except that the added amount of TEPA was changed to 8.2 g.

(Measurement of Amino Group Content of Water-Insoluble Material 7 Included in Material 7 for Blood Purification)

The same operation as for Material 1 for Blood Purification was carried out to measure the amino group content of Water-insoluble Material 7 included in Material 7 for Blood Purification. The results are shown in Table 5.

(Measurement of Amide Group Content of Water-Insoluble Material 7 Included in Material 7 for Blood Purification)

The same operation as for Material 1 for Blood Purification was carried out to measure the amide group content of Water-insoluble Material 7 included in Material 7 for Blood Purification. The results are shown in Table 5.

(Preparation of Material 8 for Blood Purification)

Knitted Fabric 8 which was a material for blood purification (hereinafter referred to as Material 8 for Blood Purification) was obtained by carrying out the same operation as for Material 3 for Blood Purification except that the added amount of NMCA was changed to 4.6 g.

(Measurement of Amino Group Content of Water-Insoluble Material 8 Included in Material 8 for Blood Purification)

The same operation as for Material 1 for Blood Purification was carried out to measure the amino group content of Water-insoluble Material 8 included in Material 8 for Blood Purification. The results are shown in Table 5.

(Measurement of Amide Group Content of Water-Insoluble Material 8 Included in Material 8 for Blood Purification)

The same operation as for Material 1 for Blood Purification was carried out to measure the amide group content of Water-insoluble Material 8 included in Material 8 for Blood Purification. The results are shown in Table 5.

(Preparation of Material 9 for Blood Purification)

Knitted Fabric 9 which was a material for blood purification (hereinafter referred to as Material 9 for Blood Purification) was obtained by carrying out the same operation as for Material 8 for Blood Purification except that the added amount of TEPA was changed to 0.25 g.

(Measurement of Amino Group Content of Water-Insoluble Material 9 Included in Material 9 for Blood Purification)

The same operation as for Material 1 for Blood Purification was carried out to measure the amino group content of Water-insoluble Material 9 included in Material 9 for Blood Purification. The results are shown in Table 5.

(Measurement of Amide Group Content of Water-Insoluble Material 9 Included in Material 9 for Blood Purification)

The same operation as for Material 1 for Blood Purification was carried out to measure the amide group content of Water-insoluble Material 9 included in Material 9 for Blood Purification. The results are shown in Table 5.

(Preparation of Material 10 for Blood Purification)

Knitted Fabric 10 which was a material for blood purification (hereinafter referred to as Material 10 for Blood Purification) was obtained by carrying out the same operation as for Material 8 for Blood Purification except that the added amount of TEPA was changed to 0.82 g.

(Measurement of Amino Group Content of Water-Insoluble Material 10 Included in Material 10 for Blood Purification)

The same operation as for Material 1 for Blood Purification was carried out to measure the amino group content of Water-insoluble Material 10 included in Material 10 for Blood Purification. The results are shown in Table 5.

(Measurement of Amide Group Content of Water-Insoluble Material 10 Included in Material 10 for Blood Purification)

The same operation as for Material 1 for Blood Purification was carried out to measure the amide group content of Water-insoluble Material 10 included in Material 10 for Blood Purification. The results are shown in Table 5.

(Preparation of Material 11 for Blood Purification)

Knitted Fabric 11 which was a material for blood purification (hereinafter referred to as Material 11 for Blood Purification) was obtained by carrying out the same operation as for Material 8 for Blood Purification except that the added amount of TEPA was changed to 3.3 g.

(Measurement of Amino Group Content of Water-Insoluble Material 11 Included in Material 11 for Blood Purification)

The same operation as for Material 1 for Blood Purification was carried out to measure the amino group content of Water-insoluble Material 11 included in Material 11 for Blood Purification. The results are shown in Table 5.

(Measurement of Amide Group Content of Water-Insoluble Material 11 Included in Material 11 for Blood Purification)

The same operation as for Material 1 for Blood Purification was carried out to measure the amide group content of Water-insoluble Material 11 included in Material 11 for Blood Purification. The results are shown in Table 5.

(Preparation of Material 12 for Blood Purification)

Knitted Fabric 12 which was a material for blood purification (hereinafter referred to as Material 12 for Blood Purification) was obtained by carrying out the same operation as for Material 8 for Blood Purification except that the added amount of TEPA was changed to 8.2 g.

(Measurement of Amino Group Content of Water-Insoluble Material 12 Included in Material 12 for Blood Purification)

The same operation as for Material 1 for Blood Purification was carried out to measure the amino group content of Water-insoluble Material 12 included in Material 12 for Blood Purification. The results are shown in Table 5.

(Measurement of Amide Group Content of Water-Insoluble Material 12 Included in Material 12 for Blood Purification)

The same operation as for Material 1 for Blood Purification was carried out to measure the amide group content of Water-insoluble Material 12 included in Material 12 for Blood Purification. The results are shown in Table 5.

(Preparation of Material 13 for Blood Purification)

Knitted Fabric 13 which was a material for blood purification (hereinafter referred to as Material 13 for Blood Purification) was obtained by carrying out the same operation as for Material 8 for Blood Purification except that the time during which Knitted Fabric B was impregnated with a solution mixture of the NMCA solution and the PFA solution was changed to four hours and that the added amount of TEPA was changed to 0.08 g.

(Measurement of Amino Group Content of Water-Insoluble Material 13 Included in Material 13 for Blood Purification)

The same operation as for Material 1 for Blood Purification was carried out to measure the amino group content of Water-insoluble Material 13 included in Material 13 for Blood Purification. The results are shown in Table 5.

(Measurement of Amide Group Content of Water-Insoluble Material 13 Included in Material 13 for Blood Purification)

The same operation as for Material 1 for Blood Purification was carried out to measure the amide group content of Water-insoluble Material 13 included in Material 13 for Blood Purification. The results are shown in Table 5.

(Preparation of Material 14 for Blood Purification)

Knitted Fabric 14 which was a material for blood purification (hereinafter referred to as Material 14 for Blood Purification) was obtained by carrying out the same operation as for Material 13 for Blood Purification except that the added amount of TEPA was changed to 0.12 g.

(Measurement of Amino Group Content of Water-Insoluble Material 14 Included in Material 14 for Blood Purification)

The same operation as for Material 1 for Blood Purification was carried out to measure the amino group content of Water-insoluble Material 14 included in Material 14 for Blood Purification. The results are shown in Table 5.

(Measurement of Amide Group Content of Water-Insoluble Material 14 Included in Material 14 for Blood Purification)

The same operation as for Material 1 for Blood Purification was carried out to measure the amide group content of Water-insoluble Material 14 included in Material 14 for Blood Purification. The results are shown in Table 5.

(Preparation of Material 15 for Blood Purification)

Knitted Fabric 15 which was a material for blood purification (hereinafter referred to as Material 15 for Blood Purification) was obtained by carrying out the same operation as for Material 13 for Blood Purification except that the added amount of TEPA was changed to 0.41 g.

(Measurement of Amino Group Content of Water-Insoluble Material 15 Included in Material 15 for Blood Purification)

The same operation as for Material 1 for Blood Purification was carried out to measure the amino group content of Water-insoluble Material 15 included in Material 15 for Blood Purification. The results are shown in Tables 5, 6, and 10.

(Measurement of Amide Group Content of Water-Insoluble Material 15 Included in Material 15 for Blood Purification)

The same operation as for Material 1 for Blood Purification was carried out to measure the amide group content of Water-insoluble Material 15 included in Material 15 for Blood Purification. The results are shown in Tables 5, 6, and 10.

(Measurement of Phenyl Group Content of Water-Insoluble Material 15 Included in Material 15 for Blood Purification)

Water-insoluble Material 15 included in Material 15 for Blood Purification did not undergo a reaction in which a phenyl group was introduced, and accordingly the phenyl group content was regarded as 0 mmol/g.

(Measurement of Opening Ratio of Material 15 for Blood Purification)

The opening ratio of Material 15 for Blood Purification was calculated in accordance with the following method. The results are shown in Table 10.

1. Material 15 for Blood Purification was photographed using an optical microscope at a magnification ratio of 10×.

2. An image editing software (for example, "Photoshop Elements 14" available from Adobe Inc.) was launched, and the following operations were carried out in this order.

(1) A file of an image photographed using an optical microscope was opened.

(2) A part the opening ratio of which needed to be determined was cut out at 512 pixels×512 pixels (262144 pixels).

(3) Using Lighting for image adjustment, corrections were made on the opening portions and the portions of Material 15 for Blood Purification in the image ('Lighten Shadow' and 'Midtone Contrast' in Shadow/Highlights were adjusted to 100%; 'Contrast' in 'Brightness/Contrast' was adjusted to 100; and 'Brightness' was adjusted to 10).

(4) If parts of the opening portions and the portions of Material 15 for Blood Purification were uncorrected, the uncorrected parts of the opening portions and the uncorrected parts of the portions of Material for 15 Blood Purification were painted black and white respectively using the Brush tool in the drawing menu.

(5) The image was binarized by correcting the color tone in the filter into two-gradation. The value was corrected in comparison with the image yet to be corrected into two-gradation. The black portions and the white portions were made as the opening portions and the portions of Material 15 for Blood Purification respectively.

(6) The histogram in the window was opened, and the ratio of the black portions to the whole portions was regarded as an opening ratio (%).

(Preparation of Material 16 for Blood Purification)

Knitted Fabric 16 which was a material for blood purification (hereinafter referred to as Material 16 for Blood Purification) was obtained by carrying out the same operation as for Material 13 for Blood Purification except that the added amount of TEPA was changed to 0.82 g.

(Measurement of Amino Group Content of Water-Insoluble Material 16 Included in Material 16 for Blood Purification)

The same operation as for Material 1 for Blood Purification was carried out to measure the amino group content of Water-insoluble Material 16 included in Material 16 for Blood Purification. The results are shown in Table 5.

(Measurement of Amide Group Content of Water-Insoluble Material 16 Included in Material 16 for Blood Purification)

The same operation as for Material 1 for Blood Purification was carried out to measure the amide group content of Water-insoluble Material 16 included in Material 16 for Blood Purification. The results are shown in Table 5.

(Preparation of Material 17 for Blood Purification)

Knitted Fabric 17 which was a material for blood purification (hereinafter referred to as Material 17 for Blood Purification) was obtained by carrying out the same operation as for Material 13 for Blood Purification except that the added amount of TEPA was changed to 1.64 g.

(Measurement of Amino Group Content of Water-Insoluble Material 17 Included in Material 17 for Blood Purification)

The same operation as for Material 1 for Blood Purification was carried out to measure the amino group content of Water-insoluble Material 17 included in Material 17 for Blood Purification. The results are shown in Table 5.

(Measurement of Amide Group Content of Water-Insoluble Material 17 Included in Material 17 for Blood Purification)

The same operation as for Material 1 for Blood Purification was carried out to measure the amide group content of Water-insoluble Material 17 included in Material 17 for Blood Purification. The results are shown in Table 5.

(Preparation of Material 18 for Blood Purification)

Knitted Fabric 18 which was a material for blood purification (hereinafter referred to as Material 18 for Blood Purification) was obtained by carrying out the same operation as for Material 8 for Blood Purification except that the time during which Knitted Fabric B was impregnated with a solution mixture of the NMCA solution and the PFA solution was changed to 24 hours and that the added amount of TEPA was changed to 0.04 g.

(Measurement of Amino Group Content of Water-Insoluble Material 18 Included in Material 18 for Blood Purification)

The same operation as for Material 1 for Blood Purification was carried out to measure the amino group content of Water-insoluble Material 18 included in Material 18 for Blood Purification. The results are shown in Table 5.

(Measurement of Amide Group Content of Water-Insoluble Material 18 Included in Material 18 for Blood Purification)

The same operation as for Material 1 for Blood Purification was carried out to measure the amide group content of Water-insoluble Material 18 included in Material 18 for Blood Purification. The results are shown in Table 5.

(Preparation of Material 19 for Blood Purification)

Knitted Fabric 19 which was a material for blood purification (hereinafter referred to as Material 19 for Blood Purification) was obtained by carrying out the same operation as for Material 18 for Blood Purification except that the added amount of TEPA was changed to 0.12 g.

(Measurement of Amino Group Content of Water-Insoluble Material 19 Included in Material 19 for Blood Purification)

The same operation as for Material 1 for Blood Purification was carried out to measure the amino group content of Water-insoluble Material 19 included in Material 19 for Blood Purification. The results are shown in Table 5.

(Measurement of Amide Group Content of Water-Insoluble Material 19 Included in Material 19 for Blood Purification)

The same operation as for Material 1 for Blood Purification was carried out to measure the amide group content of Water-insoluble Material 19 included in Material 19 for Blood Purification. The results are shown in Table 5.

(Preparation of Material 20 for Blood Purification)

Knitted Fabric 20 which was a material for blood purification (hereinafter referred to as Material 20 for Blood Purification) was obtained by carrying out the same operation as for Material 18 for Blood Purification except that the added amount of TEPA was changed to 0.41 g.

(Measurement of Amino Group Content of Water-Insoluble Material 20 Included in Material 20 for Blood Purification)

The same operation as for Material 1 for Blood Purification was carried out to measure the amino group content of Water-insoluble Material 20 included in Material 20 for Blood Purification. The results are shown in Table 5.

(Measurement of Amide Group Content of Water-Insoluble Material 20 Included in Material 20 for Blood Purification)

The same operation as for Material 1 for Blood Purification was carried out to measure the amide group content of Water-insoluble Material 20 included in Material 20 for Blood Purification. The results are shown in Table 5.

(Preparation of Material 21 for Blood Purification)

Knitted Fabric 21 which was a material for blood purification (hereinafter referred to as Material 21 for Blood Purification) was obtained by carrying out the same operation as for Material 18 for Blood Purification except that the added amount of TEPA was changed to 0.82 g.

(Measurement of Amino Group Content of Water-Insoluble Material 21 Included in Material 21 for Blood Purification)

The same operation as for Material 1 for Blood Purification was carried out to measure the amino group content of Water-insoluble Material 21 included in Material 21 for Blood Purification. The results are shown in Table 5.

(Measurement of Amide Group Content of Water-Insoluble Material 21 Included in Material 21 for Blood Purification)

The same operation as for Material 1 for Blood Purification was carried out to measure the amide group content of Water-insoluble Material 21 included in Material 21 for Blood Purification. The results are shown in Table 5.

(Preparation of Material 22 for Blood Purification)

Knitted Fabric 22 which was a material for blood purification (hereinafter referred to as Material 22 for Blood Purification) was obtained by carrying out the same operation as for Material 18 for Blood Purification except that the added amount of TEPA was changed to 1.64 g.

(Measurement of Amino Group Content of Water-Insoluble Material 22 Included in Material 22 for Blood Purification)

The same operation as for Material 1 for Blood Purification was carried out to measure the amino group content of Water-insoluble Material 22 included in Material 22 for Blood Purification. The results are shown in Table 5.

(Measurement of Amide Group Content of Water-Insoluble Material 22 Included in Material 22 for Blood Purification)

The same operation as for Material 1 for Blood Purification was carried out to measure the amide group content of Water-insoluble Material 22 included in Material 22 for Blood Purification. The results are shown in Table 5.

(Preparation of Material 23 for Blood Purification)

NMCA in an amount of 4.6 g was added to a solution mixture of 31 g of nitrobenzene and 31 g of 98 wt % sulfuric acid, and the resulting mixture was stirred at 10° C. until the NMCA was dissolved in the solution, to obtain an NMCA solution. Then, 0.2 g of PFA was added to a solution mixture of 2.0 g of nitrobenzene and 2.0 g of 98 wt % sulfuric acid, and the resulting mixture was stirred at 20° C. until the PFA was dissolved in the solution, to obtain a PFA solution. The PFA solution in an amount of 4.2 g was cooled to 5° C. and mixed with 64.3 g of the NMCA solution, the resulting mixture was stirred for five minutes, 1 g of Knitted Fabric B was added to the mixture to be impregnated with the mixture for four hours. The impregnated Knitted Fabric B was immersed in 200 mL of 0° C. nitrobenzene to thereby terminate the reaction, and the nitrobenzene attached to the Fabric was removed by extraction with methanol.

TEPA in an amount of 0.24 g and triethylamine in an amount of 2.1 g were dissolved in 51 g of DMSO, and to this solution, the Knitted Fabric B obtained after the removal by extraction with methanol was added as it was. The Fabric was impregnated with the solution at 40° C. for three hours. The Knitted Fabric was collected on a glass filter by filtration, and washed with 500 mL of DMSO.

To 47 g of DMSO that was preliminarily dried by dehydration with activated molecular sieves 3A, 0.075 g of p-chlorophenyl isocyanate was added under a nitrogen atmosphere, the resulting mixture was heated to 30° C., and all the amount of the washed Knitted Fabric B was impregnated with the mixture for one hour. The Knitted Fabric was collected on a glass filter by filtration to obtain Knitted Fabric 23 which was a material for blood purification (hereinafter referred to as Material 23 for Blood Purification).

(Measurement of Amino Group Content of Water-Insoluble Material 23 Included in Material 23 for Blood Purification)

The same operation as for Material 1 for Blood Purification was carried out to measure the amino group content of Water-insoluble Material 23 included in Material 23 for Blood Purification. The results are shown in Table 6.

(Measurement of Amide Group Content of Water-Insoluble Material 23 Included in Material 23 for Blood Purification)

The same operation as for Material 1 for Blood Purification was carried out to measure the amide group content of Water-insoluble Material 23 included in Material 23 for Blood Purification. The results are shown in Table 6.

(Measurement of p-Chlorophenyl Group Content of Water-Insoluble Material 23 Included in Material 23 for Blood Purification)

The p-chlorophenyl group content of Water-insoluble Material 23 included in Material 23 for Blood Purification was measured by hydrolyzing the linker included in Water-insoluble Material 23 and quantitating the eluted p-chloroaniline. The details will be described below.

Four 2 cm$^2$ sheets were cut out of Water-insoluble Material 23, and the sheets were dried and measured for dry weight. Then, 4 mL of 6 M hydrochloric acid and the cut-out four sheets of Material were added to a pressure glass bottle, followed by heating at 110° C. for 20 hours. After 20 hours, 1 mL of the solution was taken out of the pressure glass bottle and transferred into a sample tube. To the sample tube, 12 mL of 0.5 M hydrochloric acid containing 5 mg of sodium nitrate, 12 mL of a 0.5 wt % TWEEN20 aqueous solution containing 36 mg of ammonium sulfamate, 12 mL of a 0.5 wt % TWEEN20 aqueous solution containing 8 mg of 1-naphthylethylenediamine-dihydrochloride were sequentially added to color the resulting mixture red. The obtained red solution was measured for absorbance at 545 nm. An aqueous solution having a known p-chloroaniline concentration was colored in the same manner to prepare a calibration curve, with which the concentration of the p-chloroaniline in the solution after hydrolysis was quantitated. Furthermore, the p-chlorophenyl group content was calculated using Equation 3. The results are shown in Table 6.

$$p\text{-Chlorophenyl Group Content (mmol/g)}=p\text{-Chloroaniline Concentration in Solution after Hydrolysis (mmol/mL)} \times \text{Amount of Solution after Hydrolysis (4 mL)} \times \text{Measurement Solution Dilute Strength (37-fold)/Dry Weight of Added Water-insoluble Material (g)} \qquad \text{Equation 3}$$

(Preparation of Material 24 for Blood Purification)

Knitted Fabric 24 which was a material for blood purification (hereinafter referred to as Material 24 for Blood Purification) was obtained by carrying out the same operation as for Material 23 for Blood Purification except that the added amount of TEPA was changed from 0.24 g to 0.36 g and the added amount of p-chlorophenyl isocyanate was changed from 0.075 g to 1.5 g.

(Measurement of Amino Group Content of Water-Insoluble Material 24 Included in Material 24 for Blood Purification)

The same operation as for Material 1 for Blood Purification was carried out to measure the amino group content of Water-insoluble Material 24 included in Material 24 for Blood Purification. The results are shown in Table 6.

(Measurement of Amide Group Content of Water-Insoluble Material 24 Included in Material 24 for Blood Purification)

The same operation as for Material 1 for Blood Purification was carried out to measure the amide group content of Water-insoluble Material 24 included in Material 24 for Blood Purification. The results are shown in Table 6.

(Measurement of p-Chlorophenyl Group Content of Water-Insoluble Material 24 Included in Material 24 for Blood Purification)

The same operation as for Material 23 for Blood Purification was carried out to measure the p-chlorophenyl group content of Water-insoluble Material 24 included in Material 24 for Blood Purification. The results are shown in Table 6.

(Preparation of Material 25 for Blood Purification)

Knitted Fabric 25 which was a material for blood purification (hereinafter referred to as Material 25 for Blood Purification) was obtained by carrying out the same operation as for Material 24 for Blood Purification except that the added p-chlorophenyl isocyanate was changed to p-chlorobenzoyl chloride.

(Measurement of Amino Group Content of Water-Insoluble Material 25 Included in Material 25 for Blood Purification)

The same operation as for Material 1 for Blood Purification was carried out to measure the amino group content of Water-insoluble Material 25 included in Material 25 for Blood Purification. The results are shown in Table 6.

(Measurement of Amide Group Content of Water-Insoluble Material 25 Included in Material 25 for Blood Purification)

The same operation as for Material 1 for Blood Purification was carried out to measure the amide group content of Water-insoluble Material 25 included in Material 25 for Blood Purification. The results are shown in Table 6.

(Measurement of p-Chlorophenyl Group Content of Water-Insoluble Material 25 Included in Material 25 for Blood Purification)

The p-chlorophenyl group content of Water-insoluble Material 25 included in Material 25 for Blood Purification was measured by hydrolyzing the linker included in Water-insoluble Material 25 and quantitating the eluted p-chlorobenzoic acid. The details will be described below.

Four 6 cm$^2$ sheets were cut out of Water-insoluble Material 25, and the sheets were dried and measured for weight. Then, 4 mL of 6M hydrochloric acid and the cut-out four sheets of Material were added to a pressure glass bottle, followed by heating at 110° C. for 20 hours. After 20 hours, all the amount of the solution was taken out of the pressure glass bottle and transferred into a sample tube. The sample tube was dried under vacuum, and a solution of 5 mM chloroform dissolved in 1 mL of dimethyl sulfoxide-d$_6$ was added to the sample tube to dissolve the residue. The solution was measured by $^1$H NMR, and the p-chlorophenyl group content was calculated using Equation 4 from the ratio of the value of integral of the peak derived from p-chlorobenzoic acid (δ=7.4 to 7.8 ppm) to the value of integral of the peak derived from chloroform (δ=7.3 ppm). The results are shown in Table 6.

p-Chlorophenyl Group Content (mmol/g)=Chloroform Concentration (5 mM)×(Value of Integral of Peak Derived from p-Chlorobenzoic Acid/ Value of Integral of Peak Derived from Chloroform)×Number of Protons Derived from Aromatic Ring of p-Chlorobenzoic Acid (4)×Liquid Amount of Dimethyl Sulfoxide-d$_6$ (1 mL)/ Weight of Water-insoluble Material 25 (g)    Equation 4

(Preparation of Material 26 for Blood Purification)

Knitted Fabric 26 which was a material for blood purification (hereinafter referred to as Material 26 for Blood Purification) was obtained by carrying out the same operation as for Material 23 for Blood Purification except that the added amount of p-chlorophenyl isocyanate was changed from 1.5 g to 0.02 g.

(Measurement of Amino Group Content of Water-Insoluble Material 26 Included in Material 26 for Blood Purification)

The same operation as for Material 1 for Blood Purification was carried out to measure the amino group content of Water-insoluble Material 26 included in Material 26 for Blood Purification. The results are shown in Table 6.

(Measurement of Amide Group Content of Water-Insoluble Material 26 Included in Material 26 for Blood Purification)

The same operation as for Material 1 for Blood Purification was carried out to measure the amide group content of Water-insoluble Material 26 included in Material 26 for Blood Purification. The results are shown in Table 6.

(Measurement of p-Chlorophenyl Group Content of Water-Insoluble Material 26 Included in Material 26 for Blood Purification)

The same operation as for Material 23 for Blood Purification was carried out to measure the p-chlorophenyl group content of Water-insoluble Material 26 included in Material 26 for Blood Purification. The results are shown in Table 6.

(Preparation of Material 27 for Blood Purification)

Knitted Fabric 27 which was a material for blood purification (hereinafter referred to as Material 27 for Blood Purification) was obtained by carrying out the same operation as for Material 23 for Blood Purification except that the added amount of p-chlorophenyl isocyanate was changed from 1.5 g to 0.1 g.

(Measurement of Amino Group Content of Water-Insoluble Material 27 Included in Material 27 for Blood Purification)

The same operation as for Material 1 for Blood Purification was carried out to measure the amino group content of Water-insoluble Material 27 included in Material 27 for Blood Purification. The results are shown in Table 6.

(Measurement of Amide Group Content of Water-Insoluble Material 27 Included in Material 27 for Blood Purification)

The same operation as for Material 1 for Blood Purification was carried out to measure the amide group content of Water-insoluble Material 27 included in Material 27 for Blood Purification. The results are shown in Table 6.

(Measurement of p-Chlorophenyl Group Content of Water-Insoluble Material 27 Included in Material 27 for Blood Purification)

The same operation as for Material 23 for Blood Purification was carried out to measure the p-chlorophenyl group content of Water-insoluble Material 27 included in Material 27 for Blood Purification. The results are shown in Table 6.

(Preparation of Material 28 for Blood Purification)

Knitted Fabric 28 which was a material for blood purification (hereinafter referred to as Material 28 for Blood Purification) was obtained by carrying out the same operation as for Material 24 for Blood Purification except that the added amount of p-chlorophenyl isocyanate was changed from 1.5 g to 0.5 g.

(Measurement of Amino Group Content of Water-Insoluble Material 28 Included in Material 28 for Blood Purification)

The same operation as for Material 1 for Blood Purification was carried out to measure the amino group content of Water-insoluble Material 28 included in Material 28 for Blood Purification. The results are shown in Table 6.

(Measurement of Amide Group Content of Water-Insoluble Material 28 Included in Material 28 for Blood Purification)

The same operation as for Material 1 for Blood Purification was carried out to measure the amide group content of Water-insoluble Material 28 included in Material 28 for Blood Purification. The results are shown in Table 6.

(Measurement of p-Chlorophenyl Group Content of Water-Insoluble Material 28 Included in Material 28 for Blood Purification)

The same operation as for Material 23 for Blood Purification was carried out to measure the p-chlorophenyl group content of Water-insoluble Material 28 included in Material 28 for Blood Purification. The results are shown in Table 6.

(Preparation of Material 29 for Blood Purification)

Knitted Fabric 29 which was a material for blood purification (hereinafter referred to as Material 29 for Blood Purification) was obtained by carrying out the same operation as for Material 23 for Blood Purification except that the added amount of TEPA was changed from 0.24 g to 0.56 g and the added amount of p-chlorophenyl isocyanate was changed from 0.075 g to 2.5 g.

(Measurement of Amino Group Content of Water-Insoluble Material 29 Included in Material 29 for Blood Purification)

The same operation as for Material 1 for Blood Purification was carried out to measure the amino group content of Water-insoluble Material 29 included in Material 29 for Blood Purification. The results are shown in Table 6.

(Measurement of Amide Group Content of Water-Insoluble Material 29 Included in Material 29 for Blood Purification)

The same operation as for Material 1 for Blood Purification was carried out to measure the amide group content of Water-insoluble Material 29 included in Material 29 for Blood Purification. The results are shown in Table 6.

(Measurement of p-Chlorophenyl Group Content of Water-Insoluble Material 29 Included in Material 29 for Blood Purification)

The same operation as for Material 23 for Blood Purification was carried out to measure the p-chlorophenyl group content of Water-insoluble Material 29 included in Material 29 for Blood Purification. The results are shown in Table 6.

(Preparation of Material 30 for Blood Purification)

Knitted Fabric 30 which was a material for blood purification (hereinafter referred to as Material 30 for Blood Purification) was obtained by carrying out the same operation as for Material 13 for Blood Purification except that the added amount of TEPA was changed to 0.82 mL of a 6 M ammonia aqueous solution.

(Measurement of Amino Group Content of Water-Insoluble Material 30 Included in Material 30 for Blood Purification)

The same operation as for Material 1 for Blood Purification was carried out to measure the amino group content of Water-insoluble Material 30 included in Material 30 for Blood Purification. The results are shown in Table 7.

(Measurement of Amide Group Content of Water-Insoluble Material 30 Included in Material 30 for Blood Purification)

The same operation as for Material 1 for Blood Purification was carried out to measure the amide group content of Water-insoluble Material 30 included in Material 30 for Blood Purification. The results are shown in Table 7.

(Preparation of Material 31 for Blood Purification)

Knitted Fabric 31 which was a material for blood purification (hereinafter referred to as Material 31 for Blood Purification) was obtained by carrying out the same operation as for Material 13 for Blood Purification except that the added amount of TEPA was changed to 0.44 g of diethylenetriamine.

(Measurement of Amino Group Content of Water-Insoluble Material 31 Included in Material 31 for Blood Purification)

The same operation as for Material 1 for Blood Purification was carried out to measure the amino group content of Water-insoluble Material 31 included in Material 31 for Blood Purification. The results are shown in Table 7.

(Measurement of Amide Group Content of Water-Insoluble Material 31 Included in Material 31 for Blood Purification)

The same operation as for Material 1 for Blood Purification was carried out to measure the amide group content of Water-insoluble Material 31 included in Material 31 for Blood Purification. The results are shown in Table 7.

(Preparation of Material 32 for Blood Purification)

Knitted Fabric 32 which was a material for blood purification (hereinafter referred to as Material 32 for Blood Purification) was obtained by carrying out the same operation as for Material 13 for Blood Purification except that the added amount of TEPA was changed to 0.50 g of polyethyleneimine (having a weight average molecular weight of 600).

(Measurement of Amino Group Content of Water-Insoluble Material 32 Included in Material 32 for Blood Purification)

The same operation as for Material 1 for Blood Purification was carried out to measure the amino group content of Water-insoluble Material 32 included in Material 32 for Blood Purification. The results are shown in Table 7.

(Measurement of Amide Group Content of Water-Insoluble Material 32 Included in Material 32 for Blood Purification)

The same operation as for Material 1 for Blood Purification was carried out to measure the amide group content of Water-insoluble Material 32 included in Material 32 for Blood Purification. The results are shown in Table 7.

(Preparation of Material 33 for Blood Purification)

Knitted Fabric 33 which was a material for blood purification (hereinafter referred to as Material 33 for Blood Purification) was obtained by carrying out the same operation as for Material 15 for Blood Purification except that the knitted fabric used was changed from Knitted Fabric A to Knitted Fabric C.

(Measurement of Amino Group Content of Water-Insoluble Material 33 Included in Material 33 for Blood Purification)

The same operation as for Material 1 for Blood Purification was carried out to measure the amino group content of Water-insoluble Material 33 included in Material 33 for Blood Purification. The results are shown in Table 10.

(Measurement of Amide Group Content of Water-Insoluble Material 33 Included in Material 33 for Blood Purification)

The same operation as for Material 1 for Blood Purification was carried out to measure the amide group content of Water-insoluble Material 33 included in Material 33 for Blood Purification. The results are shown in Table 10.

(Measurement of Opening Ratio of Material 33 for Blood Purification)

The same operation as for Material 15 for Blood Purification was carried out to calculate the opening ratio of Material 33 for Blood Purification. The results are shown in Table 10.

(Preparation of Material 34 for Blood Purification)

Knitted Fabric 34 which was a material for blood purification (hereinafter referred to as Material 34 for Blood Purification) was obtained by carrying out the same operation as for Material 15 for Blood Purification except that the knitted fabric used was changed from Knitted Fabric A to Knitted Fabric D.

(Measurement of Amino Group Content of Water-Insoluble Material 34 Included in Material 34 for Blood Purification)

The same operation as for Material 1 for Blood Purification was carried out to measure the amino group content of Water-insoluble Material 34 included in Material 34 for Blood Purification. The results are shown in Table 10.

(Measurement of Amide Group Content of Water-Insoluble Material 34 Included in Material 34 for Blood Purification)

The same operation as for Material 1 for Blood Purification was carried out to measure the amide group content of Water-insoluble Material 34 included in Material 34 for Blood Purification. The results are shown in Table 10.

(Measurement of Opening Ratio of Material 34 for Blood Purification)

The same operation as for Material 33 for Blood Purification was carried out to calculate the opening ratio of Material 34 for Blood Purification. The results are shown in Table 10.

(Preparation of Material 35 for Blood Purification)

Knitted Fabric 35 which was a material for blood purification (hereinafter referred to as Material 35 for Blood Purification) was obtained by carrying out the same operation as for Material 15 for Blood Purification except that the knitted fabric used was changed from Knitted Fabric A to Knitted Fabric E.

(Measurement of Amino Group Content of Water-Insoluble Material 35 Included in Material 35 for Blood Purification)

The same operation as for Material 1 for Blood Purification was carried out to measure the amino group content of Water-insoluble Material 35 included in Material 35 for Blood Purification. The results are shown in Table 10.

(Measurement of Amide Group Content of Water-Insoluble Material 35 Included in Material 35 for Blood Purification)

The same operation as for Material 1 for Blood Purification was carried out to measure the amide group content of Water-insoluble Material 35 included in Material 35 for Blood Purification. The results are shown in Table 10.

(Measurement of Opening Ratio of Material 35 for Blood Purification) The same operation as for Material 33 for Blood Purification was carried out to calculate the opening ratio of Material 35 for Blood Purification. The results are shown in Table 10.

(Preparation of Material 36 for Blood Purification)

Knitted Fabric 36 which was a material for blood purification (hereinafter referred to as Material 36 for Blood Purification) was obtained by carrying out the same operation as for Material 15 for Blood Purification except that the knitted fabric used was changed from Knitted Fabric A to Knitted Fabric F.

(Measurement of Amino Group Content of Water-Insoluble Material 36 Included in Material 36 for Blood Purification)

The same operation as for Material 1 for Blood Purification was carried out to measure the amino group content of Water-insoluble Material 36 included in Material 36 for Blood Purification. The results are shown in Table 10.

(Measurement of Amide Group Content of Water-Insoluble Material 36 Included in Material 36 for Blood Purification)

The same operation as for Material 1 for Blood Purification was carried out to measure the amide group content of Water-insoluble Material 36 included in Material 36 for Blood Purification. The results are shown in Table 10.

(Measurement of Opening Ratio of Material 36 for Blood Purification)

The same operation as for Material 33 for Blood Purification was carried out to calculate the opening ratio of Material 36 for Blood Purification. The results are shown in Table 10.

(Preparation of Material 37 for Blood Purification)

A solution mixture of 21 mL of nitrobenzene and 42 mL of 98 wt % sulfuric acid was cooled to 5° C., 5.7 g of NMCA was added to and dissolved in the solution mixture, 1 L of cold nitrobenzene was added to the resulting mixture, and to the obtained mixture, a solution of 2 g of Udel polysulfone P3500 (a polymer having a weight average molecular weight of 30000) dissolved in 1 L of nitrobenzene was added with sufficient stirring. Then, the resulting mixture was further stirred at 5° C. for three hours. Thereafter, the reaction mixture was put in a large excess of cold methanol, and the precipitate was washed well with methanol and dried to obtain 2 g of amidemethylated polysulfone.

In a solution of 1 g of the amidemethylated polysulfone dissolved in 50 mL of DMF, 6 g of a knitted fabric that was composed of a polypropylene fiber having a single yarn diameter of 1 μm and a total fineness of 97 dtex and had a dry weight of 0.0095 g/cm$^2$ and a bulk density of 0.33 g/cm$^3$ was immersed for four hours. Then, the knitted fabric was dehydrated by centrifugation to obtain a coating knitted fabric.

TEPA in an amount of 0.32 g and triethylamine in an amount of 2.1 g were dissolved in 51 g of DMSO, and to this solution, the coating knitted fabric was added as it was. The fabric was impregnated in the solution at 40° C. for three hours. The Knitted Fabric was collected on a glass filter by filtration, washed with 500 mL of DMSO, 3 L of distilled water, and physiological saline to obtain Knitted Fabric 37 which was a material for blood purification (hereinafter referred to as Material 37 for Blood Purification).

(Measurement of Amino Group Content of Water-Insoluble Material 37 Included in Material 37 for Blood Purification)

The same operation as for Material 1 for Blood Purification was carried out to measure the amino group content of Water-insoluble Material 37 Included in Material 37 for Blood Purification. The results are shown in Table 11.

(Measurement of Amide Group Content of Water-Insoluble Material 37 Included in Material 37 for Blood Purification)

The same operation as for Material 1 for Blood Purification was carried out to measure the amide group content of Water-insoluble Material 37 included in Material 37 for Blood Purification. The results are shown in Table 11.

Example 1

To confirm the blood purification performance of Material 9 for Blood Purification, Material 9 for Blood Purification was impregnated in a cytokine solution for a predetermined time and then taken out, followed by measuring a reduction in the amount of the cytokines in the solution between before and after the impregnation. The measurement method will be described below.

Material 9 for Blood Purification was cut into disks having a diameter of 6 mm, and four of the disks were put into a polypropylene container. To this container, fetal bovine serum (hereinafter referred to as FBS) prepared so as to have interleukin-6 (hereinafter referred to as IL-6) and interleukin-8 (hereinafter referred to as IL-8) each having a concentration of 2000 pg/mL, which are each one kind of cytokine, was added so as to make up 30 mL per 1 cm$^3$ of the Material for Blood Purification, and the resultant was mixed by inversion in an incubator at 37° C. for two hours, followed by measuring each of the IL-6 and the IL-8 in the FBS for concentration by ELISA. The IL-6 adsorption rate and the IL-8 adsorption rate were calculated from the IL-6 concentration and the IL-8 concentration measured before the mixing by inversion, using the following Equation 5 and Equation 6. The results are shown in Table 5.

IL-6 Adsorption Rate of Material 1 for Blood Purification (%)=100×{IL-6 Concentration Measured before Mixing by Inversion (pg/mL)/IL-6 Concentration Measured after Mixing by Inversion (pg/mL)}  Equation 5

IL-8 Adsorption Rate of Material 1 for Blood Purification (%)=100×{IL-8 Concentration Measured before Mixing by Inversion (pg/mL)/IL-8 Concentration Measured after Mixing by Inversion (pg/mL)}   Equation 6

Example 2

For Material 10 for Blood Purification, the same operation as in Example 1 was carried out to calculate the IL-6 adsorption rate and the IL-8 adsorption rate. The results are shown in Table 5.

Example 3

For Material 11 for Blood Purification, the same operation as in Example 1 was carried out to calculate the IL-6 adsorption rate and the IL-8 adsorption rate. The results are shown in Table 5.

Example 4

For Material 14 for Blood Purification, the same operation as in Example 1 was carried out to calculate the IL-6 adsorption rate and the IL-8 adsorption rate. The results are shown in Table 5.

Example 5

For Material 15 for Blood Purification, the same operation as in Example 1 was carried out to calculate the IL-6 adsorption rate and the IL-8 adsorption rate. The results are shown in Table 5.

Example 6

For Material 16 for Blood Purification, the same operation as in Example 1 was carried out to calculate the IL-6 adsorption rate and the IL-8 adsorption rate. The results are shown in Table 5.

Example 7

For Material 19 for Blood Purification, the same operation as in Example 1 was carried out to calculate the IL-6 adsorption rate and the IL-8 adsorption rate. The results are shown in Table 5.

Example 8

For Material 20 for Blood Purification, the same operation as in Example 1 was carried out to calculate the IL-6 adsorption rate and the IL-8 adsorption rate. The results are shown in Table 5.

Example 9

For Material 21 for Blood Purification, the same operation as in Example 1 was carried out to calculate the IL-6 adsorption rate and the IL-8 adsorption rate. The results are shown in Table 5.

Example 10

To check the platelet adhesion rate of Material 15 for Blood Purification, 50 mL of blood was drawn from a healthy volunteer to collect heparin (the heparin concentration: 30 U/mL), followed by carrying out the following measurement.

Material 15 for Blood Purification was cut into disks having a diameter of 8 mm, and six of the disks were loaded into a polypropylene container. Furthermore, LPS and heparin (hereinafter referred to as HP) were added to the blood at 37° C. for one hour (the LPS concentration: 70 EU/mL, the HP concentration), and the resulting mixture was added to the container, followed by mixing by inversion. Before and after the blood was brought in contact with Material for Blood Purification, the number of platelets was measured using a sequential multi-channel blood cell analyzer, followed by calculating the platelet adhesion rate using the following Equation 7. The results are shown in Table 6.

Platelet Adhesion Rate (%)=(Platelets in Blood Measured after Platelet Adsorption Test)/(Platelets in Blood Measured before Platelet Adsorption Test)   Equation 7

Example 11

For Material 23 for Blood Purification, the same operation as in Example 1 was carried out to calculate the IL-6 adsorption rate and the IL-8 adsorption rate. Further, for Material 23 for Blood Purification, the same operation as in Example 10 was carried out to calculate the platelet adhesion rate. The results are shown in Table 6.

Example 12

For Material 24 for Blood Purification, the same operation as in Example 1 was carried out to calculate the IL-6 adsorption rate and the IL-8 adsorption rate. Further, for Material 24 for Blood Purification, the same operation as in Example 10 was carried out to calculate the platelet adhesion rate. The results are shown in Table 6.

Example 13

For Material 25 for Blood Purification, the same operation as in Example 1 was carried out to calculate the IL-6 adsorption rate and the IL-8 adsorption rate. Further, for Material 25 for Blood Purification, the same operation as in Example 10 was carried out to calculate the platelet adhesion rate. The results are shown in Table 6.

Example 14

For Material 26 for Blood Purification, the same operation as in Example 1 was carried out to calculate the IL-6 adsorption rate and the IL-8 adsorption rate. Further, for Material 26 for Blood Purification, the same operation as in Example 10 was carried out to calculate the platelet adhesion rate. The results are shown in Table 6.

Example 15

For Material 27 for Blood Purification, the same operation as in Example 1 was carried out to calculate the IL-6 adsorption rate and the IL-8 adsorption rate. Further, for Material 27 for Blood Purification, the same operation as in Example 10 was carried out to calculate the platelet adhesion rate. The results are shown in Table 6.

Example 16

For Material 28 for Blood Purification, the same operation as in Example 1 was carried out to calculate the IL-6 adsorption rate and the IL-8 adsorption rate. Further, for Material 28 for Blood Purification, the same operation as in Example 10 was carried out to calculate the platelet adhesion rate. The results are shown in Table 6.

Example 17

For Material 29 for Blood Purification, the same operation as in Example 1 was carried out to calculate the IL-6 adsorption rate and the IL-8 adsorption rate. Further, for Material 29 for Blood Purification, the same operation as in Example 10 was carried out to calculate the platelet adhesion rate. The results are shown in Table 6.

Example 18

For Material 30 for Blood Purification, the same operation as in Example 1 was carried out to calculate the IL-6 adsorption rate and the IL-8 adsorption rate. The results are shown in Table 7.

Example 19

For Material 31 for Blood Purification, the same operation as in Example 1 was carried out to calculate the IL-6 adsorption rate and the IL-8 adsorption rate. The results are shown in Table 7.

Example 20

For Material 32 for Blood Purification, the same operation as in Example 1 was carried out to calculate the IL-6 adsorption rate and the IL-8 adsorption rate. The results are shown in Table 7.

Example 21

To confirm the blood purification performance of Material 14 for Blood Purification in more detail, a removal rate of each of an activated granulocyte-activated platelet complex, an activated monocyte-activated platelet complex, an activated granulocyte, and an activated monocyte was measured. The measurement method will be described below.

Disks, 1 cm in diameter, cut out of Material 14 for Blood Purification for Example 21 were loaded in the form of a laminate in a cylindrical column having a solution inlet and a solution outlet at the top and bottom (1 cm in inside diameter×1.2 cm in height, 0.94 cm³ in volume, 2 cm in outside diameter, made of polycarbonate), to thereby prepare a column including Material 14 for Blood Purification for Example 21. LPS was added to blood of a healthy human volunteer to become 70 EU/mL, the resulting blood was shaken at 65 rpm at 37° C. for 30 minutes, the activated blood was allowed to pass through the column at a flow rate of 0.63 mL/min, and blood samples were taken at the inlet and outlet of the column. Assuming that the blood flowed into the column at a time point of 0 minute, a sample was taken out at the column outlet when the blood had passed through the column for 3.5 to 6.5 minutes. The cell surface antigens of the samples obtained after the blood was allowed to pass through the column were stained with a fluorescently-labeled antibody shown in Table 8, and then the samples were subjected to hemolysis using VersaLyse, left to stand, cooled on ice, and stored in a dark place, followed by promptly measuring the number of cells contained in each sample. In this regard, 7-AAD Viability Staining Solution (Biolegend) was used to discriminate living cells, and Flow Count (BECKMAN COULTER) was used to count the number of cells. For measurement, flow cytometry (BD Cytometer Setup and Tracking Beads (Becton, Dickinson and Company)) was used. For analysis, BD FACS Diva software Version 6.1.3 (Becton, Dickinson and Company) or FLOWJO (available from Tomy Digital Biology Co., Ltd.) was used. The concentrations of an activated granulocyte-activated platelet complex, an activated monocyte-activated platelet complex, an activated granulocyte, and an activated monocyte were calculated, followed by calculating the respective removal rates before the entry into and after the exiting out of the column, using the following Equation 8 to Equation 11. The results are shown in Table 9.

Activated Granulocyte Removal Rate (%)={(Activated Granulocyte Concentration at Column Inlet Side)−(Activated Granulocyte Concentration at Column Outlet Side)}/(Activated Granulocyte Concentration at Column Inlet Side)×100    Equation 8

Activated Granulocyte-Activated Platelet Complex Removal Rate (%)={(Activated Granulocyte-Activated Platelet Complex Concentration at Column Inlet Side)−(Activated Granulocyte-Activated Platelet Complex Concentration at Column Outlet Side)}/(Activated Granulocyte-Activated Platelet Complex Concentration at Column Inlet Side)×100    Equation 9

Activated Monocyte Removal Rate (%)={(Activated Monocyte Concentration at Column Inlet Side)−(Activated Monocyte Concentration at Column Outlet Side)}/(Activated Monocyte Concentration at Column Inlet Side)×100    Equation 10

Activated Monocyte-Activated Platelet Complex Removal Rate (%)={(Activated Monocyte-Activated Platelet Complex Concentration at Column Inlet Side)}−(Activated Monocyte-Activated Platelet Complex Concentration at Column Outlet Side)/(Activated Monocyte-Activated Platelet Complex Concentration at Column Inlet Side)×100    Equation 11

Example 22

For Material 15 for Blood Purification, the same operation as in Example 21 was carried out to calculate a removal rate of each of an activated granulocyte, an activated granulocyte-activated platelet complex, an activated monocyte, and an activated monocyte-activated platelet complex. The results are shown in Table 9.

Example 23

For Material 16 for Blood Purification, the same operation as in Example 21 was carried out to calculate a removal rate of each of an activated granulocyte, an activated granulocyte-activated platelet complex, an activated monocyte, and an activated monocyte-activated platelet complex. The results are shown in Table 9.

Example 24

For Material 23 for Blood Purification, the same operation as in Example 21 was carried out to calculate a removal rate of each of an activated granulocyte, an activated granulocyte-activated platelet complex, an activated monocyte, and an activated monocyte-activated platelet complex. The results are shown in Table 9.

Example 25

For Material 24 for Blood Purification, the same operation as in Example 21 was carried out to calculate a removal rate of each of an activated granulocyte, an activated granulocyte-activated platelet complex, an activated monocyte, and an activated monocyte-activated platelet complex. The results are shown in Table 9.

Example 26

For Material 25 for Blood Purification, the same operation as in Example 21 was carried out to calculate a removal rate of each of an activated granulocyte, an activated granulocyte-activated platelet complex, an activated monocyte, and an activated monocyte-activated platelet complex. The results are shown in Table 9.

Example 27

For Material 26 for Blood Purification, the same operation as in Example 21 was carried out to calculate a removal rate of each of an activated granulocyte, an activated granulocyte-activated platelet complex, an activated monocyte, and an activated monocyte-activated platelet complex. The results are shown in Table 9.

Example 28

For Material 27 for Blood Purification, the same operation as in Example 21 was carried out to calculate a removal rate of each of an activated granulocyte, an activated granulocyte-activated platelet complex, an activated monocyte, and an activated monocyte-activated platelet complex. The results are shown in Table 9.

Example 29

For Material 28 for Blood Purification, the same operation as in Example 21 was carried out to calculate a removal rate of each of an activated granulocyte, an activated granulocyte-activated platelet complex, an activated monocyte, and an activated monocyte-activated platelet complex. The results are shown in Table 9.

Example 30

For Material 29 for Blood Purification, the same operation as in Example 21 was carried out to calculate a removal rate of each of an activated granulocyte, an activated granulocyte-activated platelet complex, an activated monocyte, and an activated monocyte-activated platelet complex. The results are shown in Table 9.

Example 31

Simulated blood was used to measure a pressure loss of Material 33 for Blood Purification. Disks, 1 cm in diameter, cut out of Material 33 for Blood Purification were loaded in the form of a laminate in a cylindrical column having a solution inlet and a solution outlet at the top and bottom (1 cm in inside diameter×1.2 cm in height, 0.94 cm$^3$ in volume, 2 cm in outside diameter, made of polycarbonate), to thereby prepare a column in which the disks had a bulk density of 0.30 g/cm$^3$. Simulated blood (a 50 wt % glycerin aqueous solution) whose temperature was kept at 37° C. (outside temperature) was allowed to pass through each column at a flow rate of 0.65 mL/min, followed by measuring the inlet pressure and outlet pressure of the column. In this regard, the flow rate was set in accordance with the calculation: 100 mL/min/145 cm$^3$×0.94 cm$^3$=0.65 mL/min. A value obtained by subtracting the outlet pressure value at a time point of ten minutes after the start of blood passing from the inlet pressure value at a time point of ten minutes after the start of blood passing was calculated as a simulated blood pressure loss. The results are shown in Table 10.

Example 32

For Material 34 for Blood Purification, the same operation as in Example 31 was carried out to measure a pressure loss using simulated blood, followed by calculating a simulated blood pressure loss. The results are shown in Table 10.

Example 33

For Material 15 for Blood Purification, the same operation as in Example 31 was carried out to measure a pressure loss using simulated blood, followed by calculating a simulated blood pressure loss. The results are shown in Table 10.

Example 34

For Material 35 for Blood Purification, the same operation as in Example 31 was carried out to measure a pressure loss using simulated blood, followed by calculating a simulated blood pressure loss. The results are shown in Table 10.

Example 35

For Material 36 for Blood Purification, the same operation as in Example 31 was carried out to measure a pressure loss using simulated blood, followed by calculating a simulated blood pressure loss. The results are shown in Table 10.

Example 36

For Material 37 for Blood Purification, the same operations as in Example 1 and Example 21 were carried out to calculate the IL-6 adsorption rate, the IL-8 adsorption rate, and a removal rate of each of an activated granulocyte-activated platelet complex, an activated monocyte-activated platelet complex, an activated granulocyte, and an activated monocyte. The results are shown in Table 11.

Comparative Example 1

For Material 1 for Blood Purification, the same operation as in Example 1 was carried out to calculate the IL-6 adsorption rate and the IL-8 adsorption rate. The results are shown in Table 5.

Comparative Example 2

For Material 2 for Blood Purification, the same operation as in Example 1 was carried out to calculate the IL-6 adsorption rate and the IL-8 adsorption rate. The results are shown in Table 5.

Comparative Example 3

For Material 3 for Blood Purification, the same operation as in Example 1 was carried out to calculate the IL-6 adsorption rate and the IL-8 adsorption rate. The results are shown in Table 5.

Comparative Example 4

For Material 4 for Blood Purification, the same operation as in Example 1 was carried out to calculate the IL-6 adsorption rate and the IL-8 adsorption rate. The results are shown in Table 5.

Comparative Example 5

For Material 5 for Blood Purification, the same operation as in Example 1 was carried out to calculate the IL-6 adsorption rate and the IL-8 adsorption rate. The results are shown in Table 5.

Comparative Example 6

For Material 6 for Blood Purification, the same operation as in Example 1 was carried out to calculate the IL-6 adsorption rate and the IL-8 adsorption rate. The results are shown in Table 5.

Comparative Example 7

For Material 7 for Blood Purification, the same operation as in Example 1 was carried out to calculate the IL-6 adsorption rate and the IL-8 adsorption rate. The results are shown in Table 5.

Comparative Example 8

For Material 8 for Blood Purification, the same operation as in Example 1 was carried out to calculate the IL-6 adsorption rate and the IL-8 adsorption rate. The results are shown in Table 5.

Comparative Example 9

For Material 12 for Blood Purification, the same operation as in Example 1 was carried out to calculate the IL-6 adsorption rate and the IL-8 adsorption rate. The results are shown in Table 5.

Comparative Example 10

For Material 13 for Blood Purification, the same operation as in Example 1 was carried out to calculate the IL-6 adsorption rate and the IL-8 adsorption rate. The results are shown in Table 5.

Comparative Example 11

For Material 17 for Blood Purification, the same operation as in Example 1 was carried out to calculate the IL-6 adsorption rate and the IL-8 adsorption rate. The results are shown in Table 5.

Comparative Example 12

For Material 18 for Blood Purification, the same operation as in Example 1 was carried out to calculate the IL-6 adsorption rate and the IL-8 adsorption rate. The results are shown in Table 5.

Comparative Example 13

For Material 22 for Blood Purification, the same operation as in Example 1 was carried out to calculate the IL-6 adsorption rate and the IL-8 adsorption rate. The results are shown in Table 5.

Comparative Example 14

For Material 17 for Blood Purification, the same operation as in Example 21 was carried out to calculate a removal rate of each of an activated granulocyte-activated platelet complex, an activated monocyte-activated platelet complex, an activated granulocyte, and an activated monocyte. The results are shown in Table 9.

TABLE 5

|  |  | Amide Group Content (mmol/g) | Amino Group Content (mmol/g) | IL-6 Adsorption Rate | IL-8 Adsorption Rate |
|---|---|---|---|---|---|
| Example 1 | Material 9 for Blood Purification | 3.0 | 1.0 | 66% | 70% |
| Example 2 | Material 10 for Blood Purification | 3.0 | 4.3 | 80% | 80% |
| Example 3 | Material 11 for Blood Purification | 3.0 | 6.7 | 70% | 70% |
| Example 4 | Material 14 for Blood Purification | 4.7 | 1.1 | 80% | 97% |
| Example 5 | Material 15 for Blood Purification | 4.7 | 3.8 | 92% | 95% |
| Example 6 | Material 16 for Blood Purification | 4.7 | 6.1 | 80% | 88% |
| Example 7 | Material 19 for Blood Purification | 7.0 | 1.4 | 80% | 88% |
| Example 8 | Material 20 for Blood Purification | 7.0 | 4.9 | 80% | 97% |
| Example 9 | Material 21 for Blood Purification | 7.0 | 6.9 | 51% | 56% |
| Comparative Example 1 | Material 1 for Blood Purification | 1.5 | 2.3 | 2% | 6% |
| Comparative Example 2 | Material 2 for Blood Purification | 1.1 | 2.3 | 2% | 6% |
| Comparative Example 3 | Material 3 for Blood Purification | 2.7 | 0.8 | 0% | 5% |
| Comparative Example 4 | Material 4 for Blood Purification | 2.7 | 1.2 | 4% | 8% |

TABLE 5-continued

|  |  | Amide Group Content (mmol/g) | Amino Group Content (mmol/g) | IL-6 Adsorption Rate | IL-8 Adsorption Rate |
|---|---|---|---|---|---|
| Comparative Example 5 | Material 5 for Blood Purification | 2.7 | 4.0 | 2% | 6% |
| Comparative Example 6 | Material 6 for Blood Purification | 2.7 | 6.5 | 3% | 4% |
| Comparative Example 7 | Material 7 for Blood Purification | 2.7 | 7.5 | 4% | 13% |
| Comparative Example 8 | Material 8 for Blood Purification | 3.0 | 0.9 | 34% | 45% |
| Comparative Example 9 | Material 12 for Blood Purification | 3.0 | 7.3 | 20% | 35% |
| Comparative Example 10 | Material 13 for Blood Purification | 4.7 | 0.6 | 35% | 55% |
| Comparative Example 11 | Material 17 for Blood Purification | 4.7 | 7.2 | 12% | 33% |
| Comparative Example 12 | Material 18 for Blood Purification | 7.0 | 0.9 | 38% | 42% |
| Comparative Example 13 | Material 22 for Blood Purification | 7.0 | 7.9 | 18% | 0% |

It is evident from the results in Table 5 that the material for blood purification according to the present application has excellent blood purification performance.

TABLE 6

|  |  | Amide Group Content (mmol/g) | Amino Group Content (mmol/g) | Phenyl Group Content (mmol/g) | IL-6 Adsorption Rate | IL-8 Adsorption Rate | Platelet Adhesion Rate |
|---|---|---|---|---|---|---|---|
| Example 10 | Material 15 for Blood Purification | 4.7 | 3.8 | 0 | 92% | 95% | 83% |
| Example 11 | Material 23 for Blood Purification | 4.7 | 3.8 | 0.02 | 92% | 95% | 78% |
| Example 12 | Material 24 for Blood Purification | 4.7 | 3.8 | 1.0 | 92% | 95% | 75% |
| Example 13 | Material 25 for Blood Purification | 4.7 | 3.8 | 1.0 | 92% | 95% | 75% |
| Example 14 | Material 26 for Blood Purification | 4.7 | 3.8 | 0.01 | 93% | 96% | 79% |
| Example 15 | Material 27 for Blood Purification | 4.7 | 3.8 | 005 | 94% | 97% | 79% |
| Example 16 | Material 28 for Blood Purification | 4.7 | 3.8 | 0.3 | 93% | 95% | 75% |
| Example 17 | Material 29 for Blood Purification | 4.7 | 3.8 | 2.5 | 91% | 93% | 72% |

It is evident from the results in Table 6 that, according to the present application, introducing a phenyl group(s) into the material for blood purification makes it possible to inhibit adhesion of platelets further.

TABLE 7

|  |  | Amide Group Content (mmol/g) | Amino Group Content (mmol/g) | IL-6 Removal Rate | IL-8 Removal Rate |
|---|---|---|---|---|---|
| Example 18 | Material 30 for Blood Purification | 4.7 | 3.2 | 95% | 98% |

TABLE 7-continued

|  |  | Amide Group Content (mmol/g) | Amino Group Content (mmol/g) | IL-6 Removal Rate | IL-8 Removal Rate |
|---|---|---|---|---|---|
| Example 19 | Material 31 for Blood Purification | 4.7 | 3.4 | 90% | 96% |
| Example 20 | Material 32 for Blood Purification | 4.7 | 3.0 | 84% | 95% |

It is evident from the results in Table 7 that the material for blood purification according to the present application, whose amino group structure may vary, exerts excellent blood purification performance.

TABLE 8

| Antibody Name | Manufacturer | Catalog No. |
|---|---|---|
| APC Mouse Anti-Human CD11b (activated) | BioLegend | 301410 |
| PE/Cy7 Mouse Anti-Human CD14 | BioLegend | 556619 |
| BV510 Mouse Anti-Human CD45 | BioLegend | 304036 |
| BV421 Mouse | BioLegend | 304926 |

TABLE 8-continued

| Antibody Name | Manufacturer | Catalog No. |
|---|---|---|
| Anti-Human CD62P FITC Mouse | BioLegend | 557749 |
| Anti-Human CD66b APC Mouse | BD Biosciences | 340442 |
| IgG1 Isotype Control PE/Cy7 Mouse | BioLegend | 400232 |
| IgG2a Isotype Control BV510 Mouse | BioLegend | 400172 |
| IgG1 Isotype Control BV421 Mouse | BioLegend | 400158 |
| IgG1 κ,Isotype Control FITC Mouse | BD Biosciences | 349041 |
| IgM Isotype Control |  |  |

TABLE 9

|  |  | Amide Group Content (mmol/g) | Amino Group Content (mmol/g) | Phenyl Group Content (mmol/g) | Activated Granulocyte Removal Rate | Activated Granulocyte-Activated Platelet Complex Removal Rate | Activated Monocyte Removal Rate | Activated Monocyte-Activated Platelet Complex Removal Rate |
|---|---|---|---|---|---|---|---|---|
| Example 21 | Material 14 for Blood Purification | 4.7 | 1.1 | 0 | 20% | 52% | 30% | 58% |
| Example 22 | Material 15 for Blood Purification | 4.7 | 3.8 | 0 | 22% | 55% | 33% | 63% |
| Example 23 | Material 16 for Blood Purification | 4.7 | 6.1 | 0 | 12% | 8% | 15% | 13% |
| Example 24 | Material 23 for Blood Purification | 4.7 | 3.8 | 0.02 | 23% | 56% | 34% | 68% |
| Example 25 | Material 24 for Blood Purification | 4.7 | 3.8 | 1.0 | 27% | 61% | 35% | 70% |
| Example 26 | Material 25 for Blood Purification | 4.7 | 3.8 | 1.0 | 26% | 58% | 36% | 69% |
| Example 27 | Material 26 for Blood Purification | 4.7 | 3.8 | 0.01 | 24% | 59% | 33% | 66% |
| Example 28 | Material 27 for Blood Purification | 4.7 | 3.8 | 0.05 | 26% | 58% | 36% | 69% |
| Example 29 | Material 28 for Blood Purification | 4.7 | 3.8 | 0.3 | 26% | 58% | 36% | 69% |
| Example 30 | Material 29 for Blood Purification | 4.7 | 3.8 | 2.5 | 28% | 60% | 36% | 70% |
| Comparative Example 14 | Material 17 for Blood Purification | 4.7 | 7.2 | 0 | 5% | 1% | 0% | 2% |

It is evident from the results in Table 9 that the amino group content and phenyl group content of the material for blood purification according to the present application can be controlled to remove an activated granulocyte, an activated granulocyte-activated platelet complex, an activated monocyte, and an activated monocyte-activated platelet complex.

TABLE 10

| | | Amide Group Content (mmol/g) | Amino Group Content (mmol/g) | Opening Ratio | Simulated Blood Pressure Loss (mmHg) |
|---|---|---|---|---|---|
| Example 31 | Material 33 for Blood Purification | 4.7 | 3.7 | 0.1% | 45 |
| Example 32 | Material 34 for Blood Purification | 4.7 | 3.8 | 1.2% | 28 |
| Example 33 | Material 15 for Blood Purification | 4.7 | 3.8 | 8.3% | 3 |
| Example 34 | Material 35 for Blood Purification | 4.7 | 3.9 | 13.2% | 9 |
| Example 35 | Material 36 for Blood Purification | 4.7 | 4.0 | 30.0% | 19 |

It is evident from the results in Table 10 that the material for blood purification according to the present application can perform blood purification with a low pressure loss.

TABLE 11

| | | Amide Group Content (mmol/g) | Amino Group Content (mmol/g) | IL-6 Removal Rate | IL-8 Removal Rate | Activated Granulocyte Removal Rate | Activated Granulocyte-Activated Platelet Complex Removal Rate | Activated Monocyte Removal Rate | Activated Monocyte-Activated Platelet Complex Removal Rate |
|---|---|---|---|---|---|---|---|---|---|
| Example 36 | Material 37 for Blood Purification | 4.7 | 5.8 | 53% | 58% | 15% | 11% | 18% | 22% |

It is evident from the results in Table 11 that the material for blood purification according to the present application exerts excellent blood purification performance independent of the kind of the substrate.

INDUSTRIAL APPLICABILITY

The material for blood purification according to the present invention can be used for purification of blood components in medical fields, particularly for removal of cytokines and activated leukocyte-activated platelet complexes.

REFERENCE SIGNS LIST

1. Material for Blood Purification (Knitted Fabric)
2. Fiber (Black Portions)
3. Opening Portions (White Portions)
4. Column
5. Simulated Blood or Human Blood that is yet to pass through Column
6. Simulated Blood or Human Blood that has passed through Column
7. Circuit
8. Inlet Pressure Measurement Device
9. Outlet Pressure Measurement Device
10. Pump
11. Constant Temperature Water Bath
12. Heater

The invention claimed is:

1. A material for blood purification, the material comprising a water-insoluble material in which a ligand having an amide group(s) and an amino group(s) is bound to a substrate, wherein the content of the amide group(s) is 3.0 to 7.0 mmol per 1 g dry weight of the water-insoluble material;

wherein the content of the amino group(s) is 1.0 to 7.0 mmol per 1 g dry weight of the water-insoluble material;

wherein the ligand having the structure represented by Formula below is bound to the substrate:

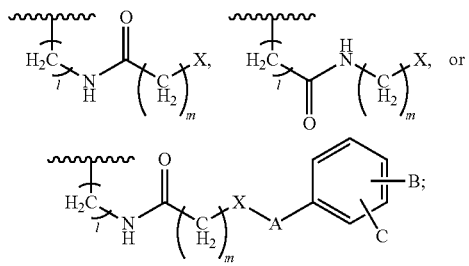

wherein l is an integer of 1 to 5, m is an integer of 1 to 5, X is a group having one or more amines as a partial structure; A is a linker; B is a hydrogen atom or halogen atom; C is a hydrogen atom or halogen atom; and the wavy line represents a position at which the ligand is bound to the substrate; and wherein the content of the phenyl group is more than 0 mmol and not more than 7.0 mmol per 1 g dry weight of the water-insoluble material.

2. The material for blood purification, according to claim 1, wherein the ligand having the structure represented by Formula (I) below is bound to the substrate:

(wherein X is a group having one or more amines as a partial structure; and the wavy line represents a position at which the ligand is bound to the substrate).

3. The material for blood purification, according to claim 2, wherein the material is in the form of a knitted fabric having an opening ratio of 0.1 to 30.0%.

4. The material for blood purification, according to claim 2, wherein the material is for removing a cytokine and an activated leukocyte-activated platelet complex.

5. The material for blood purification, according to claim 1, wherein the ligand has a phenyl group, and the ligand has the structure represented by Formula (II) below:

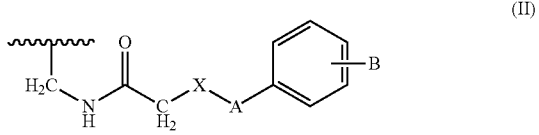

(wherein X is a group having one or more amines as a partial structure; A is a linker; B is a hydrogen atom or halogen atom; and the wavy line represents a position at which the ligand is bound to the substrate); and
wherein the content of the phenyl group is more than 0 mmol and not more than 7.0 mmol per 1 g dry weight of the water-insoluble material.

6. The material for blood purification, according to claim 5, wherein the material is in the form of a knitted fabric having an opening ratio of 0.1 to 30.0%.

7. The material for blood purification, according to claim 5, wherein the material is for removing a cytokine and an activated leukocyte-activated platelet complex.

8. The material according to claim 5, wherein the amino group(s) is a group having —NH—.

9. The material for blood purification, according to claim 1, wherein the substrate is a polystyrene or polysulfone, or a derivative thereof.

10. The material for blood purification, according to claim 1, wherein the material is in the form of fibers or particles.

11. The material for blood purification, according to claim 1, wherein the material is in the form of a knitted fabric having an opening ratio of 0.1 to 30.0%.

12. The material for blood purification, according to claim 11, wherein the material is for removing a cytokine and an activated leukocyte-activated platelet complex.

13. The material for blood purification, according to claim 1, wherein the material is for removing a cytokine and an activated leukocyte-activated platelet complex.

14. An apparatus for blood purification, the apparatus comprising the material for blood purification, according to claim 1.

15. The material according to claim 1, wherein X is a group derived from a compound having a plurality of amino groups.

16. The material according to claim 1, wherein the amino group(s) is a group having —NH— and/or —NH$_2$.

17. A method for blood purification comprising:
contacting a quantify of blood with a material to purify the blood, said material comprising a water-insoluble material in which a ligand having an amide group(s) and an amino group(s) is bound to a substrate,
wherein the content of the amide group(s) is 3.0 to 7.0 mmol per 1 g dry weight of the water-insoluble material;
wherein the content of the amino group(s) is 1.0 to 7.0 mmol per 1 g dry weight of the water-insoluble material;
wherein the ligand having the structure represented by Formula below is bound to the substrate:

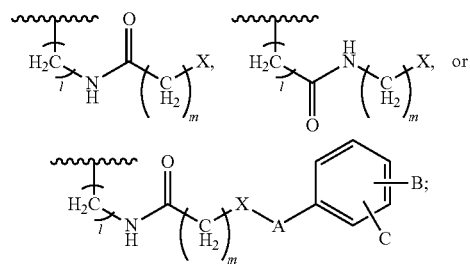

wherein l is an integer of 1 to 5, m is an integer of 1 to 5, X is a group having one or more amines as a partial structure; A is a linker; B is a hydrogen atom or halogen atom; C is a hydrogen atom or halogen atom; and the wavy line represents a position at which the ligand is bound to the substrate; and wherein the content of the phenyl group is more than 0 mmol and not more than 7.0 mmol per 1 g dry weight of the water-insoluble material.

18. The method according to claim 17, wherein the ligand having the structure represented by Formula (I) below is bound to the substrate:

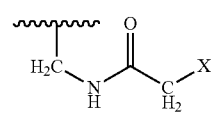

(wherein X is a group having one or more amines as a partial structure; and the wavy line represents a position at which the ligand is bound to the substrate).

19. The method according to claim 17,
wherein the ligand has a phenyl group, and the ligand has the structure represented by Formula (II) below:

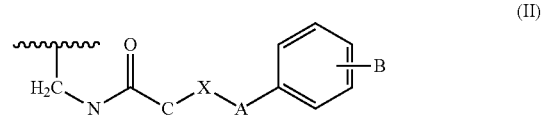

(wherein X is a group having one or more amines as a partial structure; A is a linker; B is a hydrogen atom or halogen atom; and the wavy line represents a position at which the ligand is bound to the substrate); and wherein the content of the phenyl group is more than 0 mmol and not more than 7.0 mmol per 1 g dry weight of the water-insoluble material.

20. The method according to claim 19, wherein the amino group(s) is a group having —NH—.

21. The method according to claim 17, wherein the substrate is a polystyrene or polysulfone, or a derivative thereof.

22. The method according to claim 17, wherein the material is in the form of a knitted fabric having an opening ratio of 0.1 to 30.0%.

23. The method according to claim 17, wherein X is a group derived from a compound having a plurality of amino groups.

24. The method according to claim 17, wherein the amino group(s) is a group having —NH— and/or —NH$_2$.

* * * * *